US012773344B2

(12) United States Patent
Stich et al.

(10) Patent No.: US 12,773,344 B2
(45) Date of Patent: Oct. 27, 2026

(54) COOLING/HEATING MEDICAL PAD WITH SOFTENED EDGES

(71) Applicant: C. R. Bard, Inc., Franklin Lakes, NJ (US)

(72) Inventors: Madeline Stich, Thornton, CO (US); Karthik Ganesan, Longmont, CO (US); Tyghe E. Boone-Worthman, Brighton, CO (US); Sean E. Walker, Platteville, CO (US)

(73) Assignee: C. R. Bard, Inc., Franklin Lakes, NJ (US)

( * ) Notice: Subject to any disclaimer, the term of this patent is extended or adjusted under 35 U.S.C. 154(b) by 349 days.

(21) Appl. No.: 18/274,156

(22) PCT Filed: Jan. 25, 2022

(86) PCT No.: PCT/US2022/013672
§ 371 (c)(1),
(2) Date: Jul. 25, 2023

(87) PCT Pub. No.: WO2022/159879
PCT Pub. Date: Jul. 28, 2022

(65) Prior Publication Data

US 2025/0032310 A1 Jan. 30, 2025

Related U.S. Application Data

(60) Provisional application No. 63/141,294, filed on Jan. 25, 2021.

(51) Int. Cl.
*A61F 7/08* (2006.01)
*A61F 7/00* (2006.01)

(52) U.S. Cl.
CPC ...... *A61F 7/086* (2013.01); *A61F 2007/0054* (2013.01)

(58) Field of Classification Search
CPC ............................................ A61F 2007/0054
See application file for complete search history.

(56) References Cited

U.S. PATENT DOCUMENTS 2,167,865 A 8/1939 Beecher
2,250,325 A 7/1941 Barnes
(Continued)

FOREIGN PATENT DOCUMENTS

AU 678753 B3 6/1997
AU 2007201161 B2 12/2010
(Continued)

OTHER PUBLICATIONS

U.S. Appl. No. 17/547,128, filed Dec. 9, 2021 Restriction Requirement dated Sep. 5, 2024.
(Continued)

*Primary Examiner* — Kaitlyn E Smith
(74) *Attorney, Agent, or Firm* — Rutan & Tucker LLP

(57) ABSTRACT

Disclosed herein is an apparatus and system directed to providing for a patient's comfort while undergoing Targeted Temperature Management (TTM). The apparatus and system pertain to a medical pad for exchanging thermal energy with a patient. The medical pad includes a flexible upper sheet, a flexible base member, an edge guard, and an adhesive surface. The flexible base member is interconnected to the flexible upper sheet to define a fluid containing layer between the flexible base member and the flexible upper sheet. The edge guard is situated along an edge of the flexible upper sheet, and extends outwardly from the edge of the flexible upper sheet. The adhesive surface is disposed on a skin-contacting side of the flexible upper sheet and the edge guard, and is adapted for releasable adhesive contact with skin of the patient.

30 Claims, 8 Drawing Sheets

(56) References Cited

U.S. PATENT DOCUMENTS

| | | | |
|---|---|---|---|
| 2,296,207 A | 9/1942 | Kittinger | |
| 2,595,328 A | 5/1952 | Bowen | |
| 2,602,302 A | 7/1952 | Poux | |
| 2,726,658 A | 12/1955 | Chessey | |
| 2,807,809 A | 10/1957 | Kottemann | |
| 3,075,529 A | 1/1963 | Young, Jr. | |
| 3,091,242 A | 5/1963 | Johnson et al. | |
| 3,212,286 A | 10/1965 | Curtis | |
| 3,506,013 A | 4/1970 | Zdenek | |
| 3,734,293 A | 5/1973 | Biskis | |
| 3,830,676 A | 8/1974 | Elkins | |
| 3,867,939 A | 2/1975 | Moore et al. | |
| 3,900,035 A | 8/1975 | Welch et al. | |
| 3,927,671 A | 12/1975 | Chittenden et al. | |
| 3,945,617 A | 3/1976 | Callery | |
| 3,995,621 A | 12/1976 | Fletcher et al. | |
| 4,059,293 A | 11/1977 | Sipler | |
| 4,092,982 A | 6/1978 | Salem | |
| 4,108,146 A | 8/1978 | Golden | |
| 4,114,620 A | 9/1978 | Moore et al. | |
| 4,118,946 A | 10/1978 | Tubin | |
| 4,149,541 A | 4/1979 | Gammons et al. | |
| 4,154,245 A | 5/1979 | Daily | |
| 4,161,210 A | 7/1979 | Reid et al. | |
| 4,195,631 A | 4/1980 | Baucom | |
| 4,311,022 A | 1/1982 | Hall | |
| 4,444,727 A | 4/1984 | Yanagihara et al. | |
| 4,508,123 A | 4/1985 | Wyatt et al. | |
| 4,580,408 A | 4/1986 | Stuebner | |
| 4,753,241 A | 6/1988 | Brannigan et al. | |
| 4,834,705 A | 5/1989 | Vaillancourt | |
| 4,846,176 A | 7/1989 | Golden | |
| 4,867,748 A | 9/1989 | Samuelsen | |
| 4,884,304 A | 12/1989 | Elkins | |
| 4,886,063 A | 12/1989 | Crews | |
| 4,908,248 A | 3/1990 | Nakashima et al. | |
| 4,919,134 A | 4/1990 | Streeter | |
| 4,962,761 A | 10/1990 | Golden | |
| 4,971,056 A | 11/1990 | Seacord | |
| 4,981,135 A | 1/1991 | Hardy | |
| 4,989,607 A | 2/1991 | Keusch et al. | |
| 5,000,252 A | 3/1991 | Faghri | |
| 5,005,374 A | 4/1991 | Spitler | |
| 5,050,596 A | 9/1991 | Walasek et al. | |
| 5,062,414 A | 11/1991 | Grim | |
| 5,072,875 A | 12/1991 | Zacoi | |
| 5,090,409 A | 2/1992 | Genis | |
| 5,097,829 A | 3/1992 | Quisenberry | |
| 5,111,668 A | 5/1992 | Parrish et al. | |
| 5,113,666 A | 5/1992 | Parrish et al. | |
| 5,133,348 A | 7/1992 | Mayn | |
| 5,146,625 A | 9/1992 | Steele et al. | |
| 5,154,706 A | 10/1992 | Cartmell et al. | |
| 5,190,032 A | 3/1993 | Zacoi | |
| 5,265,669 A | 11/1993 | Schneider | |
| 5,268,022 A | 12/1993 | Garrett et al. | |
| 5,289,695 A | 3/1994 | Parrish et al. | |
| 5,300,103 A | 4/1994 | Stempel et al. | |
| 5,304,213 A | 4/1994 | Berke et al. | |
| 5,304,216 A | 4/1994 | Wallace | |
| 5,320,164 A | 6/1994 | Szczesuil et al. | |
| 5,329,638 A * | 7/1994 | Hansen | A41D 13/088 2/16 |
| 5,383,919 A | 1/1995 | Kelly et al. | |
| 5,393,462 A | 2/1995 | Avery | |
| 5,405,366 A | 4/1995 | Fox et al. | |
| 5,407,421 A | 4/1995 | Goldsmith | |
| 5,409,500 A | 4/1995 | Dyrek | |
| 5,411,541 A | 5/1995 | Bell et al. | |
| 5,423,751 A | 6/1995 | Harrison et al. | |
| 5,431,622 A | 7/1995 | Pyrozyk et al. | |
| 5,437,673 A | 8/1995 | Baust et al. | |
| 5,456,701 A | 10/1995 | Stout | |
| 5,466,250 A | 11/1995 | Johnson, Jr. et al. | |
| 5,470,353 A | 11/1995 | Jensen | |
| 5,476,489 A | 12/1995 | Koewler | |
| 5,484,448 A | 1/1996 | Steele et al. | |
| 5,486,207 A | 1/1996 | Mahawili | |
| 5,514,169 A | 5/1996 | Dickerhoff et al. | |
| 5,545,194 A | 8/1996 | Augustine | |
| 5,566,413 A | 10/1996 | Webb et al. | |
| 5,605,144 A | 2/1997 | Simmons et al. | |
| 5,609,620 A | 3/1997 | Daily | |
| 5,620,482 A | 4/1997 | Augustine et al. | |
| 5,624,477 A | 4/1997 | Armond | |
| 5,634,940 A | 6/1997 | Panyard | |
| 5,640,728 A | 6/1997 | Graebe | |
| 5,645,855 A | 7/1997 | Lorenz | |
| 5,658,325 A | 8/1997 | Augustine | |
| 5,662,695 A | 9/1997 | Mason et al. | |
| 5,683,439 A | 11/1997 | Jensen | |
| 5,720,774 A | 2/1998 | Glucksman | |
| 5,733,318 A | 3/1998 | Augustine | |
| 5,755,755 A | 5/1998 | Panyard | |
| 5,785,716 A | 7/1998 | Bayron et al. | |
| 5,806,335 A | 9/1998 | Herbert et al. | |
| 5,824,025 A | 10/1998 | Augustine | |
| 5,837,002 A | 11/1998 | Augustine et al. | |
| 5,840,080 A | 11/1998 | Der Ovanesian | |
| 5,843,145 A | 12/1998 | Brink | |
| 5,871,526 A | 2/1999 | Gibbs et al. | |
| 5,879,378 A | 3/1999 | Usui | |
| 5,887,437 A | 3/1999 | Maxim | |
| 5,913,849 A | 6/1999 | Sundstrom et al. | |
| 5,947,914 A | 9/1999 | Augustine | |
| 5,948,012 A | 9/1999 | Mahaffey et al. | |
| 5,968,000 A | 10/1999 | Harrison et al. | |
| 5,986,163 A | 11/1999 | Augustine | |
| 5,989,285 A | 11/1999 | DeVilbiss et al. | |
| 6,010,528 A | 1/2000 | Augustine et al. | |
| 6,019,783 A | 2/2000 | Philips et al. | |
| 6,030,412 A | 2/2000 | Klatz et al. | |
| 6,047,106 A | 4/2000 | Salyer | |
| 6,074,415 A | 6/2000 | Der Ovanesian | |
| 6,083,256 A | 7/2000 | Der Ovanesian | |
| 6,083,418 A | 7/2000 | Czarnecki et al. | |
| 6,117,164 A | 9/2000 | Gildersleeve et al. | |
| 6,176,869 B1 | 1/2001 | Mason et al. | |
| 6,176,870 B1 | 1/2001 | Augustine | |
| 6,185,744 B1 | 2/2001 | Poholski | |
| 6,188,930 B1 | 2/2001 | Carson | |
| 6,189,149 B1 | 2/2001 | Allen | |
| 6,189,550 B1 | 2/2001 | Stickel et al. | |
| 6,197,045 B1 | 3/2001 | Carson | |
| 6,234,538 B1 | 5/2001 | Lauer | |
| 6,238,427 B1 | 5/2001 | Matta | |
| 6,255,552 B1 | 7/2001 | Cummings et al. | |
| 6,257,011 B1 | 7/2001 | Siman-Tov et al. | |
| 6,290,716 B1 | 9/2001 | Augustine | |
| 6,336,935 B1 | 1/2002 | Davis et al. | |
| 6,349,560 B1 | 2/2002 | Maier-Laxhuber et al. | |
| 6,352,550 B1 * | 3/2002 | Gildersleeve | A61F 7/02 607/108 |
| 6,364,937 B1 | 4/2002 | McMahon | |
| 6,371,976 B1 | 4/2002 | Vrzalik et al. | |
| 6,375,674 B1 | 4/2002 | Carson | |
| 6,389,839 B1 | 5/2002 | Sabin | |
| 6,436,130 B1 | 8/2002 | Philips et al. | |
| 6,451,036 B1 | 9/2002 | Heitzmann et al. | |
| 6,454,792 B1 | 9/2002 | Noda et al. | |
| 6,461,379 B1 | 10/2002 | Carson et al. | |
| 6,463,212 B1 | 10/2002 | Salyer | |
| 6,503,297 B1 | 1/2003 | Lu et al. | |
| 6,508,831 B1 | 1/2003 | Kushnir | |
| 6,508,859 B1 | 1/2003 | Zia et al. | |
| 6,511,501 B1 | 1/2003 | Augustine et al. | |
| 6,511,502 B2 | 1/2003 | Fletcher | |
| 6,517,510 B1 | 2/2003 | Stewart et al. | |
| D471,987 S | 3/2003 | Hoglund et al. | |
| D472,322 S | 3/2003 | Hoglund et al. | |
| 6,551,348 B1 | 4/2003 | Blalock et al. | |
| D474,544 S | 5/2003 | Hoglund et al. | |
| 6,559,096 B1 | 5/2003 | Smith et al. | |
| 6,584,797 B1 | 7/2003 | Smith et al. | |

(56) References Cited

U.S. PATENT DOCUMENTS

| | | | | |
|---|---|---|---|---|
| 6,589,270 | B2 | 7/2003 | Augustine | |
| 6,591,630 | B2 | 7/2003 | Smith et al. | |
| 6,601,404 | B1 | 8/2003 | Roderick | |
| 6,613,030 | B1 | 9/2003 | Coles et al. | |
| 6,620,187 | B2 | 9/2003 | Carson et al. | |
| 6,620,188 | B1 | 9/2003 | Ginsburg et al. | |
| 6,645,232 | B2 | 11/2003 | Carson | |
| 6,648,905 | B2 | 11/2003 | Hoglund et al. | |
| 6,653,607 | B2 | 11/2003 | Ellis et al. | |
| D483,125 | S | 12/2003 | Hoglund et al. | |
| 6,660,027 | B2 | 12/2003 | Gruszecki et al. | |
| 6,669,715 | B2 | 12/2003 | Hoglund et al. | |
| 6,682,525 | B2 | 1/2004 | Lalonde et al. | |
| D487,147 | S | 2/2004 | Ellingboe et al. | |
| D487,148 | S | 2/2004 | Ellingboe et al. | |
| 6,688,132 | B2 | 2/2004 | Smith et al. | |
| 6,692,518 | B2 | 2/2004 | Carson | |
| 6,699,267 | B2 | 3/2004 | Voorhees et al. | |
| 6,701,724 | B2 | 3/2004 | Smith et al. | |
| 6,743,250 | B2 | 6/2004 | Renfro | |
| 6,755,801 | B2 | 6/2004 | Utterberg et al. | |
| 6,755,852 | B2 | 6/2004 | Lachenbruch et al. | |
| D492,773 | S | 7/2004 | Ellingboe et al. | |
| 6,770,848 | B2 | 8/2004 | Haas et al. | |
| 6,799,063 | B2 | 9/2004 | Carson | |
| 6,800,087 | B2 | 10/2004 | Papay et al. | |
| 6,802,855 | B2 | 10/2004 | Ellingboe et al. | |
| 6,802,885 | B2 | 10/2004 | Luk et al. | |
| 6,818,012 | B2 | 11/2004 | Ellingboe | |
| 6,827,728 | B2 | 12/2004 | Ellingboe et al. | |
| 6,846,322 | B2 | 1/2005 | Kane et al. | |
| 6,858,068 | B2 | 2/2005 | Smith et al. | |
| 6,878,156 | B1 | 4/2005 | Noda | |
| 6,893,453 | B2 | 5/2005 | Agarwal et al. | |
| 6,904,956 | B2 | 6/2005 | Noel | |
| 6,909,074 | B1 | 6/2005 | Bradley | |
| 6,921,198 | B2 | 7/2005 | Gruszecki et al. | |
| 6,931,875 | B1 | 8/2005 | Allen et al. | |
| 6,942,644 | B2 | 9/2005 | Worthen | |
| 6,960,243 | B1 | 11/2005 | Smith et al. | |
| 6,968,711 | B2 | 11/2005 | Smith et al. | |
| 6,969,399 | B2 | 11/2005 | Schock et al. | |
| 7,008,445 | B2 | 3/2006 | Lennox | |
| 7,022,099 | B2 | 4/2006 | Litzie et al. | |
| 7,044,960 | B2 | 5/2006 | Voorhees et al. | |
| 7,052,509 | B2 | 5/2006 | Lennox et al. | |
| 7,055,575 | B2 | 6/2006 | Noel | |
| 7,056,335 | B2 | 6/2006 | Agarwal et al. | |
| 7,063,718 | B2 | 6/2006 | Dobak, III | |
| 7,077,858 | B2 | 7/2006 | Fletcher et al. | |
| 7,097,657 | B2 | 8/2006 | Noda et al. | |
| 7,101,389 | B1 | 9/2006 | Augustine et al. | |
| 7,122,047 | B2 | 10/2006 | Grahn et al. | |
| 7,160,316 | B2 | 1/2007 | Hamilton et al. | |
| 7,172,586 | B1 | 2/2007 | Dae et al. | |
| 7,240,720 | B2 | 7/2007 | Noel | |
| 7,303,554 | B2 | 12/2007 | Lalonde et al. | |
| 7,303,579 | B2 | 12/2007 | Schock et al. | |
| 7,338,516 | B2 | 3/2008 | Quincy et al. | |
| 7,361,186 | B2 | 4/2008 | Voorhees et al. | |
| 7,377,935 | B2 | 5/2008 | Schock et al. | |
| 7,507,250 | B2 | 3/2009 | Lennox | |
| 7,517,360 | B2 | 4/2009 | Frey et al. | |
| RE40,815 | E | 6/2009 | Kudaravalli et al. | |
| 7,547,320 | B2 | 6/2009 | Schook et al. | |
| RE40,868 | E | 8/2009 | Ryba et al. | |
| 7,621,944 | B2 | 11/2009 | Wilson et al. | |
| 7,621,945 | B2 | 11/2009 | Lennox et al. | |
| 7,666,213 | B2 | 2/2010 | Freedman, Jr. et al. | |
| 7,678,716 | B2 | 3/2010 | Yahiaoui et al. | |
| 7,686,840 | B2 | 3/2010 | Quincy et al. | |
| 7,727,228 | B2 | 6/2010 | Abboud et al. | |
| 7,731,739 | B2 | 6/2010 | Schock et al. | |
| 7,744,640 | B1 | 6/2010 | Faries, Jr. et al. | |
| 7,749,261 | B2 | 7/2010 | Hansen et al. | |
| 7,763,061 | B2 | 7/2010 | Schorr et al. | |
| 7,771,461 | B2 | 8/2010 | Schock et al. | |
| 7,784,304 | B2 | 8/2010 | Trinh et al. | |
| 7,799,063 | B2 | 9/2010 | Ingram et al. | |
| 7,827,815 | B2 | 11/2010 | Carson et al. | |
| 7,867,266 | B2 | 1/2011 | Collins | |
| 7,892,269 | B2 | 2/2011 | Collins et al. | |
| 7,896,910 | B2 | 3/2011 | Schirrmacher et al. | |
| 7,918,243 | B2 | 4/2011 | Diodati et al. | |
| 8,047,010 | B2 | 11/2011 | Carson et al. | |
| 8,052,624 | B2 | 11/2011 | Buchanan et al. | |
| 8,066,752 | B2 | 11/2011 | Hamilton et al. | |
| 8,182,521 | B2 | 5/2012 | Kane et al. | |
| 8,187,697 | B2 | 5/2012 | Quincy et al. | |
| 8,216,163 | B2 | 7/2012 | Edelman | |
| 8,283,602 | B2 | 10/2012 | Augustine et al. | |
| 8,454,671 | B2 | 6/2013 | Lennox et al. | |
| D685,916 | S | 7/2013 | Hoglund | |
| 8,491,644 | B1 | 7/2013 | Carson et al. | |
| 8,597,217 | B2 | 12/2013 | Lowe et al. | |
| 8,597,339 | B2 | 12/2013 | Augustine et al. | |
| 8,603,150 | B2 | 12/2013 | Kane et al. | |
| 8,632,576 | B2 | 1/2014 | Quisenberry | |
| 8,647,374 | B2 | 2/2014 | Koewler | |
| 8,715,330 | B2 | 5/2014 | Lowe et al. | |
| 8,778,119 | B2 | 7/2014 | Starr et al. | |
| 8,808,344 | B2 | 8/2014 | Scott et al. | |
| 8,840,581 | B2 | 9/2014 | McGill et al. | |
| 9,034,458 | B2 | 5/2015 | Li | |
| 9,078,742 | B2 | 7/2015 | Quincy, III et al. | |
| 9,089,462 | B1 | 7/2015 | Lafleche | |
| 9,211,358 | B2 | 12/2015 | Sinko et al. | |
| 9,278,024 | B2 | 3/2016 | Scott et al. | |
| 9,333,112 | B2 | 5/2016 | Carson | |
| 9,433,527 | B2 | 9/2016 | Varga et al. | |
| 9,552,706 | B2 | 1/2017 | Schneider, II et al. | |
| 9,566,185 | B2 | 2/2017 | Carson et al. | |
| 9,622,907 | B2 | 4/2017 | Carson et al. | |
| 9,642,404 | B2 | 5/2017 | Giles et al. | |
| 9,687,386 | B2 | 6/2017 | Carson | |
| 9,763,823 | B2 | 9/2017 | Voorhees et al. | |
| 9,907,889 | B2 | 3/2018 | Locke et al. | |
| 10,010,452 | B2 | 7/2018 | Wenske et al. | |
| 10,123,902 | B2 | 11/2018 | Carson et al. | |
| 10,220,198 | B2 | 3/2019 | Fuchs et al. | |
| 10,258,501 | B2 | 4/2019 | Carson | |
| 10,376,412 | B2 | 8/2019 | Brienza et al. | |
| 10,441,458 | B2 | 10/2019 | Voorhees et al. | |
| 10,441,707 | B2 | 10/2019 | Voorhees et al. | |
| 10,548,778 | B2 | 2/2020 | Hassenpflug et al. | |
| 10,610,424 | B1 | 4/2020 | Hoover | |
| D887,426 | S | 6/2020 | Matsushita | |
| 10,912,672 | B1 | 2/2021 | Jones et al. | |
| D922,424 | S | 6/2021 | Frueh et al. | |
| D925,574 | S | 7/2021 | Beko | |
| D928,188 | S | 8/2021 | Giannino et al. | |
| 11,173,071 | B1 | 11/2021 | Tawil et al. | |
| D939,550 | S | 12/2021 | Miyai et al. | |
| 11,234,859 | B2 | 2/2022 | Voorhees et al. | |
| D947,216 | S | 3/2022 | Leininger | |
| 11,285,039 | B2 * | 3/2022 | Steele | F24F 5/0035 |
| D948,534 | S | 4/2022 | Bessette et al. | |
| D952,666 | S | 5/2022 | Sajan | |
| D959,475 | S | 8/2022 | Norman | |
| D960,191 | S | 8/2022 | Feit et al. | |
| D973,067 | S | 12/2022 | Oh et al. | |
| 11,975,123 | B2 | 5/2024 | Appel et al. | |
| 12,193,968 | B2 | 1/2025 | Voorhees et al. | |
| 2001/0034545 | A1 | 10/2001 | Elkins | |
| 2001/0039439 | A1 | 11/2001 | Elkins et al. | |
| 2002/0007203 | A1 | 1/2002 | Gilmartin et al. | |
| 2002/0015689 | A1 | 2/2002 | Munro et al. | |
| 2002/0019657 | A1 | 2/2002 | Elkins | |
| 2002/0107558 | A1 | 8/2002 | Clifton et al. | |
| 2002/0111657 | A1 | 8/2002 | Dae et al. | |
| 2002/0138121 | A1 | 9/2002 | Fox | |
| 2002/0161419 | A1 | 10/2002 | Carson et al. | |
| 2003/0074038 | A1 | 4/2003 | Gruszecki et al. | |
| 2003/0078638 | A1 | 4/2003 | Voorhees et al. | |

(56) References Cited

U.S. PATENT DOCUMENTS

| | | | |
|---|---|---|---|
| 2003/0078639 | A1 | 4/2003 | Carson |
| 2003/0078640 | A1 | 4/2003 | Carson et al. |
| 2003/0109911 | A1 | 6/2003 | Lachenbruch et al. |
| 2003/0114903 | A1 | 6/2003 | Ellingboe |
| 2003/0135252 | A1 | 7/2003 | MacHold et al. |
| 2003/0149359 | A1 | 8/2003 | Smith |
| 2003/0149461 | A1 | 8/2003 | Johnson |
| 2003/0150232 | A1 | 8/2003 | Brudnicki |
| 2003/0163179 | A1 | 8/2003 | Hoglund et al. |
| 2003/0163180 | A1 | 8/2003 | Hoglund et al. |
| 2003/0163183 | A1 | 8/2003 | Carson |
| 2003/0163185 | A1 | 8/2003 | Carson |
| 2003/0212416 | A1 | 11/2003 | Cinelli et al. |
| 2004/0030372 | A1 | 2/2004 | Ellingboe et al. |
| 2004/0030373 | A1 | 2/2004 | Ellingboe et al. |
| 2004/0059212 | A1 | 3/2004 | Abreu |
| 2004/0064170 | A1 | 4/2004 | Radons et al. |
| 2004/0064171 | A1 | 4/2004 | Briscoe et al. |
| 2004/0073280 | A1 | 4/2004 | Dae et al. |
| 2004/0082886 | A1 | 4/2004 | Timpson |
| 2004/0087606 | A1 | 5/2004 | Voorhees et al. |
| 2004/0133253 | A1 | 7/2004 | Grahn et al. |
| 2004/0158303 | A1 | 8/2004 | Lennox et al. |
| 2004/0225341 | A1 | 11/2004 | Schock et al. |
| 2004/0243122 | A1 | 12/2004 | Auth et al. |
| 2004/0252750 | A1 | 12/2004 | Gruszecki et al. |
| 2004/0255362 | A1 | 12/2004 | Soerens et al. |
| 2004/0260369 | A1 | 12/2004 | Schock et al. |
| 2004/0267339 | A1 | 12/2004 | Yon et al. |
| 2005/0028551 | A1 | 2/2005 | Noda et al. |
| 2005/0060012 | A1 | 3/2005 | Voorhees et al. |
| 2005/0065583 | A1 | 3/2005 | Voorhees et al. |
| 2005/0096714 | A1 | 5/2005 | Freedman et al. |
| 2005/0177212 | A1 | 8/2005 | Njemanze |
| 2005/0187502 | A1 | 8/2005 | Krempel et al. |
| 2005/0244629 | A1 | 11/2005 | Usui et al. |
| 2005/0288749 | A1 | 12/2005 | Lachenbruch |
| 2006/0024053 | A1 | 2/2006 | Grant |
| 2006/0030916 | A1 | 2/2006 | Lennox |
| 2006/0036304 | A1 | 2/2006 | Cordani et al. |
| 2006/0058858 | A1 | 3/2006 | Smith |
| 2006/0069418 | A1 | 3/2006 | Schock et al. |
| 2006/0074469 | A1 | 4/2006 | Lennox et al. |
| 2006/0122673 | A1 | 6/2006 | Callister et al. |
| 2006/0124141 | A1 | 6/2006 | Dobak |
| 2006/0136023 | A1 | 6/2006 | Dobak |
| 2006/0161232 | A1 | 7/2006 | Kasza et al. |
| 2006/0190066 | A1 | 8/2006 | Worthen |
| 2006/0235114 | A1 | 10/2006 | Kitazono et al. |
| 2006/0247744 | A1 | 11/2006 | Nest et al. |
| 2006/0276089 | A1 | 12/2006 | Amarasinghe et al. |
| 2006/0287697 | A1 | 12/2006 | Lennox |
| 2006/0293734 | A1 | 12/2006 | Scott et al. |
| 2007/0016270 | A1 | 1/2007 | Stelea et al. |
| 2007/0043409 | A1 | 2/2007 | Brian et al. |
| 2007/0049997 | A1 | 3/2007 | Fields et al. |
| 2007/0054122 | A1 | 3/2007 | Paisner et al. |
| 2007/0068931 | A1 | 3/2007 | Augustine et al. |
| 2007/0073368 | A1 | 3/2007 | Cazzini et al. |
| 2007/0100404 | A1 | 5/2007 | Ko et al. |
| 2007/0173735 | A1 | 7/2007 | Callister et al. |
| 2007/0213793 | A1 | 9/2007 | Hayes |
| 2007/0225782 | A1 | 9/2007 | Taylor |
| 2007/0244475 | A1 | 10/2007 | Carson et al. |
| 2007/0270925 | A1 | 11/2007 | Levinson |
| 2008/0027523 | A1 | 1/2008 | Behringer et al. |
| 2008/0046046 | A1 | 2/2008 | Ginsburg |
| 2008/0114431 | A1 | 5/2008 | Ginsburg |
| 2008/0147152 | A1 | 6/2008 | Quincy et al. |
| 2008/0249524 | A1 | 10/2008 | Dunning |
| 2008/0255644 | A1 | 10/2008 | Carson |
| 2008/0269852 | A1 | 10/2008 | Lennox et al. |
| 2008/0275534 | A1 | 11/2008 | Noel |
| 2009/0018504 | A1 | 1/2009 | Pile-Spellman et al. |
| 2009/0043366 | A1 | 2/2009 | Dae |
| 2009/0066079 | A1 | 3/2009 | Miros et al. |
| 2009/0088825 | A1 | 4/2009 | Ota |
| 2009/0099629 | A1 | 4/2009 | Carson et al. |
| 2009/0131835 | A1 | 5/2009 | Voorhees et al. |
| 2009/0149925 | A1 | 6/2009 | MacDonald et al. |
| 2009/0157000 | A1 | 6/2009 | Waller |
| 2009/0177184 | A1 | 7/2009 | Christensen et al. |
| 2009/0182400 | A1 | 7/2009 | Dae et al. |
| 2009/0228082 | A1 | 9/2009 | Ross et al. |
| 2009/0250367 | A1 | 10/2009 | Murdoch et al. |
| 2009/0280182 | A1 | 11/2009 | Beck et al. |
| 2009/0287283 | A1 | 11/2009 | Biser et al. |
| 2009/0299287 | A1 | 12/2009 | Carson et al. |
| 2009/0312823 | A1 | 12/2009 | Patience et al. |
| 2009/0326619 | A1 | 12/2009 | Kagan |
| 2010/0016933 | A1 | 1/2010 | Chen et al. |
| 2010/0137951 | A1 | 6/2010 | Lennox et al. |
| 2010/0168825 | A1 | 7/2010 | Barbknecht |
| 2010/0198122 | A1 | 8/2010 | Freund |
| 2010/0198320 | A1 | 8/2010 | Pierre et al. |
| 2010/0204765 | A1 | 8/2010 | Hall et al. |
| 2010/0217260 | A1 | 8/2010 | Aramayo |
| 2010/0241073 | A1 | 9/2010 | Andersen et al. |
| 2010/0312160 | A1 | 12/2010 | Creighton et al. |
| 2010/0312202 | A1 | 12/2010 | Henley et al. |
| 2011/0021960 | A1 | 1/2011 | Filtvedt et al. |
| 2011/0029051 | A1 | 2/2011 | Ross |
| 2011/0045056 | A1 | 2/2011 | Munro et al. |
| 2011/0098792 | A1 | 4/2011 | Lowe et al. |
| 2011/0125238 | A1 | 5/2011 | Nofzinger |
| 2011/0152982 | A1 | 6/2011 | Richardson |
| 2011/0166633 | A1 | 7/2011 | Stull |
| 2011/0172749 | A1 | 7/2011 | Christensen et al. |
| 2011/0172750 | A1 | 7/2011 | Cassidy et al. |
| 2011/0306972 | A1 | 12/2011 | Widenhouse et al. |
| 2011/0307040 | A1 | 12/2011 | Peterson |
| 2011/0308781 | A1 | 12/2011 | O'Riordan et al. |
| 2011/0313497 | A1 | 12/2011 | Mcfarlane |
| 2012/0046720 | A1 | 2/2012 | Ishizaki |
| 2012/0065715 | A1 | 3/2012 | Carson |
| 2012/0080031 | A1 | 4/2012 | Belson |
| 2012/0095536 | A1 | 4/2012 | Machold et al. |
| 2012/0185021 | A1 | 7/2012 | Johnson et al. |
| 2012/0191035 | A1 | 7/2012 | Stephan |
| 2012/0204881 | A1 | 8/2012 | Davidson et al. |
| 2012/0220960 | A1 | 8/2012 | Ruland |
| 2013/0006335 | A1 | 1/2013 | Lowe |
| 2013/0023808 | A1 | 1/2013 | Brown et al. |
| 2013/0116760 | A1 * | 5/2013 | Carson ...................... A61F 7/10 607/104 |
| 2013/0138185 | A1 | 5/2013 | Paxman et al. |
| 2013/0190667 | A1 | 7/2013 | Kane et al. |
| 2013/0238042 | A1 | 9/2013 | Gildersleeve et al. |
| 2013/0238043 | A1 | 9/2013 | Beardall et al. |
| 2013/0310725 | A1 | 11/2013 | Jerrells et al. |
| 2014/0039451 | A1 | 2/2014 | Bangera et al. |
| 2014/0046411 | A1 | 2/2014 | Elkins et al. |
| 2014/0172050 | A1 | 6/2014 | Dabrowiak |
| 2014/0214138 | A1 | 7/2014 | Voorhees et al. |
| 2014/0222121 | A1 | 8/2014 | Spence et al. |
| 2014/0228717 | A1 | 8/2014 | Parish et al. |
| 2014/0228918 | A1 | 8/2014 | Brienza et al. |
| 2014/0276253 | A1 | 9/2014 | Varga et al. |
| 2014/0277301 | A1 | 9/2014 | Varga et al. |
| 2014/0288621 | A1 | 9/2014 | Efremkin |
| 2014/0316494 | A1 | 10/2014 | Augustine et al. |
| 2014/0343639 | A1 | 11/2014 | Hopper et al. |
| 2015/0051673 | A1 | 2/2015 | Rivas Tapia |
| 2015/0119963 | A1 | 4/2015 | Cosse |
| 2015/0173942 | A1 | 6/2015 | Whitely |
| 2015/0209174 | A1 | 7/2015 | Abreu |
| 2015/0209192 | A1 | 7/2015 | Manion et al. |
| 2015/0223972 | A1 | 8/2015 | Dabrowiak |
| 2015/0230973 | A1 | 8/2015 | Dabrowiak et al. |
| 2015/0231009 | A1 | 8/2015 | Lewis |
| 2015/0250643 | A1 | 9/2015 | Paradis |
| 2015/0290042 | A1 | 10/2015 | Freer et al. |
| 2015/0366703 | A1 | 12/2015 | Du |
| 2015/0373781 | A1 | 12/2015 | Augustine et al. |

(56) References Cited

U.S. PATENT DOCUMENTS

| | | | |
|---|---|---|---|
| 2015/0374045 | A1 | 12/2015 | Codner et al. |
| 2016/0008166 | A1 | 1/2016 | Voorhees et al. |
| 2016/0022477 | A1 | 1/2016 | Schaefer et al. |
| 2016/0038336 | A1 | 2/2016 | Hilton et al. |
| 2016/0310316 | A1 | 10/2016 | Hixson, Jr. |
| 2016/0324683 | A1 | 11/2016 | Carson |
| 2017/0049618 | A1 | 2/2017 | Ward et al. |
| 2017/0135855 | A1 | 5/2017 | Stefan et al. |
| 2017/0151087 | A1 | 6/2017 | Carson et al. |
| 2017/0189225 | A1 | 7/2017 | Voorhees et al. |
| 2017/0209305 | A1 | 7/2017 | Kaforey et al. |
| 2017/0224528 | A1 | 8/2017 | Berg et al. |
| 2017/0246029 | A1 | 8/2017 | Clark |
| 2017/0246031 | A1 | 8/2017 | Benyaminpour et al. |
| 2017/0246374 | A1 | 8/2017 | Voorhees et al. |
| 2017/0348144 | A1 | 12/2017 | Taylor et al. |
| 2017/0348145 | A1 | 12/2017 | Voorhees et al. |
| 2017/0354534 | A1 | 12/2017 | Paradis et al. |
| 2018/0000255 | A1 | 1/2018 | Youngblood et al. |
| 2018/0014967 | A1 | 1/2018 | Taylor |
| 2018/0042762 | A1 | 2/2018 | Galer |
| 2018/0042763 | A1 | 2/2018 | Galer et al. |
| 2018/0064594 | A1 | 3/2018 | Finch, Jr. et al. |
| 2018/0140407 | A1 | 5/2018 | Yoskowitz |
| 2018/0207024 | A1 | 7/2018 | Dabrowiak et al. |
| 2018/0214297 | A1 | 8/2018 | Hughett et al. |
| 2018/0214302 | A1 | 8/2018 | Dabrowiak et al. |
| 2018/0263677 | A1 | 9/2018 | Hilton et al. |
| 2018/0263748 | A1 | 9/2018 | Quinn |
| 2018/0295980 | A1 | 10/2018 | Boersma et al. |
| 2018/0376539 | A1 | 12/2018 | Augustine et al. |
| 2019/0083322 | A1 | 3/2019 | Huang et al. |
| 2019/0085644 | A1 | 3/2019 | Ames et al. |
| 2019/0117446 | A1 | 4/2019 | Carson et al. |
| 2019/0192337 | A1 | 6/2019 | Taylor et al. |
| 2019/0201574 | A1 | 7/2019 | Delury et al. |
| 2019/0262169 | A1 | 8/2019 | Vergara et al. |
| 2019/0328576 | A1 | 10/2019 | Lowe et al. |
| 2019/0331277 | A1 | 10/2019 | Vachon |
| 2020/0001022 | A1 | 1/2020 | Landy, III et al. |
| 2020/0071051 | A1 | 3/2020 | Lewis |
| 2020/0129326 | A1 | 4/2020 | Sinha et al. |
| 2020/0155341 | A1 | 5/2020 | Voorhees et al. |
| 2020/0214471 | A1 | 7/2020 | Paperno |
| 2020/0246180 | A1 | 8/2020 | Liang et al. |
| 2020/0289361 | A1 | 9/2020 | Tian et al. |
| 2020/0345971 | A1 | 11/2020 | Schirm et al. |
| 2020/0405530 | A1 | 12/2020 | Taylor et al. |
| 2021/0060230 | A1 | 3/2021 | Hopper et al. |
| 2021/0123641 | A1 | 4/2021 | Monazami et al. |
| 2022/0087874 | A1 | 3/2022 | Schneider et al. |
| 2022/0151821 | A1 | 5/2022 | Voorhees et al. |
| 2022/0192865 | A1 | 6/2022 | Hughett, Sr. et al. |
| 2022/0192867 | A1 | 6/2022 | Stich et al. |
| 2022/0233344 | A1 | 7/2022 | Hoglund |
| 2022/0233347 | A1 | 7/2022 | Canary et al. |
| 2022/0265468 | A1 | 8/2022 | Xu et al. |
| 2022/0280336 | A1 | 9/2022 | Smith et al. |
| 2022/0287875 | A1 | 9/2022 | Minchew et al. |
| 2022/0287876 | A1 | 9/2022 | Smith et al. |
| 2022/0296413 | A1 | 9/2022 | Jones |
| 2022/0296414 | A1 | 9/2022 | Bible et al. |
| 2022/0304847 | A1 | 9/2022 | Kuroda et al. |
| 2022/0313478 | A1 | 10/2022 | Johnston et al. |
| 2022/0331153 | A1 | 10/2022 | Xie et al. |
| 2022/0347009 | A1 | 11/2022 | Hughett, Sr. et al. |
| 2022/0401259 | A1 | 12/2022 | Basciano et al. |
| 2022/0406017 | A1 | 12/2022 | Wang et al. |
| 2023/0000668 | A1 | 1/2023 | Walker et al. |
| 2023/0009524 | A1 | 1/2023 | Johnston et al. |
| 2023/0011631 | A1 | 1/2023 | Yin et al. |
| 2023/0019048 | A1 | 1/2023 | Stich et al. |
| 2023/0021245 | A1 | 1/2023 | Walker et al. |
| 2023/0040583 | A1 | 2/2023 | Falis et al. |
| 2023/0077318 | A9 | 3/2023 | Voorhees et al. |
| 2023/0190519 | A1 | 6/2023 | Stich et al. |
| 2023/0346630 | A1 | 11/2023 | Lowe et al. |
| 2023/0414445 | A1 | 12/2023 | Sundar et al. |
| 2024/0065884 | A1 | 2/2024 | Fallows et al. |
| 2024/0082052 | A1 | 3/2024 | Cho et al. |
| 2024/0091054 | A1 | 3/2024 | Boone-Worthman et al. |
| 2024/0099878 | A1 | 3/2024 | Voorhees et al. |
| 2024/0108497 | A1 | 4/2024 | Daw et al. |
| 2024/0366422 | A1 | 11/2024 | Johnston et al. |
| 2025/0041107 | A1 | 2/2025 | Walker et al. |
| 2025/0110628 | A1 | 4/2025 | Litman et al. |
| 2025/0134705 | A1 | 5/2025 | Stich et al. |
| 2025/0143918 | A1 | 5/2025 | Voorhees et al. |
| 2025/0161107 | A1 | 5/2025 | Stich et al. |
| 2025/0198550 | A1 | 6/2025 | Johnston et al. |
| 2025/0332025 | A1 | 10/2025 | Brooks et al. |
| 2026/0026965 | A1 | 1/2026 | Xu et al. |
| 2026/0102279 | A1 | 4/2026 | Canary et al. |
| 2026/0174591 | A1 | 6/2026 | Johnston et al. |

FOREIGN PATENT DOCUMENTS

| | | | |
|---|---|---|---|
| CA | 2729122 | A1 | 7/2002 |
| CA | 2193385 | C | 9/2006 |
| CN | 102026596 | A | 4/2011 |
| CN | 101389372 | B | 8/2012 |
| CN | 102746518 | A | 10/2012 |
| CN | 103939695 | B | 3/2016 |
| CN | 305928532 | | 7/2020 |
| CN | 111643265 | A | 9/2020 |
| CN | 306402573 | | 3/2021 |
| CN | 113230017 | A | 8/2021 |
| CN | 307690236 | | 11/2022 |
| CN | 309180016 | | 3/2025 |
| DE | 102014118510 | A1 | 6/2016 |
| EP | 0862901 | A1 | 9/1998 |
| EP | 1073388 | A1 | 2/2001 |
| EP | 1616543 | A2 | 1/2006 |
| EP | 1641503 | A2 | 4/2006 |
| EP | 1718894 | B1 | 7/2010 |
| EP | 2204150 | A1 | 7/2010 |
| EP | 2269546 | A1 | 1/2011 |
| GB | 2118440 | A | 11/1983 |
| JP | H09508045 | A | 8/1997 |
| JP | 2002534160 | A | 10/2002 |
| JP | 2007029638 | A | 2/2007 |
| JP | 2013248293 | A | 12/2013 |
| KR | 20110020420 | A | 3/2011 |
| WO | 9807397 | A1 | 2/1998 |
| WO | 9831310 | A1 | 7/1998 |
| WO | 199944552 | A1 | 9/1999 |
| WO | 9953874 | A1 | 10/1999 |
| WO | 2000040185 | A1 | 7/2000 |
| WO | 2003086253 | A2 | 10/2003 |
| WO | 2004075949 | A2 | 9/2004 |
| WO | 2005028984 | A1 | 3/2005 |
| WO | 2005117546 | A2 | 12/2005 |
| WO | 2007120677 | A2 | 10/2007 |
| WO | 2009090403 | A1 | 7/2009 |
| WO | 2009147413 | A1 | 12/2009 |
| WO | 2009148636 | A1 | 12/2009 |
| WO | 2012125916 | A2 | 9/2012 |
| WO | 2012138980 | A2 | 10/2012 |
| WO | 2015084925 | A1 | 6/2015 |
| WO | 2016057119 | A1 | 4/2016 |
| WO | 2016123500 | A1 | 8/2016 |
| WO | 2017127768 | A1 | 7/2017 |
| WO | 2018075576 | A1 | 4/2018 |
| WO | 2022155130 | A1 | 7/2022 |
| WO | 2022155132 | A1 | 7/2022 |
| WO | 2022159513 | A1 | 7/2022 |
| WO | 2022159879 | A1 | 7/2022 |
| WO | 2022165068 | A1 | 8/2022 |
| WO | 2022235513 | A1 | 11/2022 |
| WO | 2023121674 | A1 | 6/2023 |
| WO | 2023140870 | A1 | 7/2023 |

(56) References Cited

FOREIGN PATENT DOCUMENTS

| | | | |
|---|---|---|---|
| WO | 2023154050 | A1 | 8/2023 |
| WO | 2023229609 | A1 | 11/2023 |

OTHER PUBLICATIONS

U.S. Appl. No. 17/583,090, filed Jan. 24, 2022 Restriction Requirement dated Sep. 6, 2024.
U.S. Appl. No. 17/584,101, filed Jan. 25, 2022 Restriction Requirement dated Nov. 5, 2024.
U.S. Appl. No. 17/686,301, filed Mar. 3, 2022 Non-Final Office Action dated Oct. 1, 2024.
U.S. Appl. No. 17/689,791, filed Mar. 8, 2022 Restriction Requirement dated Oct. 16, 2024.
U.S. Appl. No. 17/691,990, filed Mar. 10, 2022 Restriction Requirement dated Oct. 16, 2024.
U.S. Appl. No. 17/694,416, filed Mar. 14, 2022 Restriction Requirement dated Nov. 8, 2024.
U.S. Appl. No. 17/709,019, filed Mar. 30, 2022 Restriction Requirement dated Oct. 16, 2024.
U.S. Appl. No. 17/723,210, filed Apr. 18, 2022 Restriction Requirement dated Oct. 16, 2024.
U.S. Appl. No. 17/848,074, filed Jun. 23, 2022 Notice of Allowance dated Nov. 26, 2024.
U.S. Appl. No. 17/849,419, filed Jun. 24, 2022 Non-Final Office Action dated Nov. 8, 2024.
All in 1: Injection Tracker, posted date unavailable [online], [retrieved Apr. 10, 2025]. Retrieved from internet, https://apps.apple.com/us/app/all-in-1-injection-tracker/id1667540577. (Year: 2025).
Creating an accessible, usable and compelling Injection Site Tracking feature that can used by all our users, posted date May 2020 [u online], [retrieved Apr. 10, 2025]. Retrieved from internet, https://www.bradstricker.com/case-studies/injection-site-tracking. (Year: 2020).
Injection Tracker App, posted date unavailable [online], [retrieved Apr. 10, 2025]. Retrieved from internet, https://www.vladcristei.com/project_page_it. (Year: 2025).
U.S. Appl. No. 17/583,090, filed Jan. 24, 2022 Final Office Action dated Jul. 1, 2025.
U.S. Appl. No. 17/678,965, filed Feb. 23, 2022 Notice of Allowance dated Jun. 3, 2025.
U.S. Appl. No. 17/686,301, filed Mar. 3, 2022 Advisory Action dated Apr. 4, 2025.
U.S. Appl. No. 17/686,301, filed Mar. 3, 2022 Non-Final Office Action dated May 14, 2025.
U.S. Appl. No. 17/689,791, filed Mar. 8, 2022 Final Office Action dated May 21, 2025.
U.S. Appl. No. 17/690,908, filed Mar. 9, 2022 Final Office Action dated Jun. 24, 2025.
U.S. Appl. No. 17/694,416, filed Mar. 14, 2022 Final Office Action dated Jun. 20, 2025.
U.S. Appl. No. 17/700,216, filed Mar. 21, 2022 Final Office Action dated Jun. 23, 2025.
U.S. Appl. No. 17/709,019, filed Mar. 30, 2022 Final Office Action dated Jun. 15, 2025.
U.S. Appl. No. 17/723,210, filed Apr. 18, 2022 Final Office Action dated May 21, 2025.
U.S. Appl. No. 17/849,419, filed Jun. 24, 2022 Non-Final Office Action dated Jun. 13, 2025.
U.S. Appl. No. 17/857,997, filed Jul. 5, 2022 Non-Final Office Action dated Apr. 28, 2025.
U.S. Appl. No. 17/881,270, filed Aug. 4, 2022 Non-Final Office Action dated Apr. 28, 2025.
U.S. Appl. No. 18/085,566, filed Dec. 20, 2022 Restriction Requirement dated May 16, 2025.
U.S. Appl. No. 29/939,277, filed Apr. 25, 2024 Non-Final Office Action dated May 13, 2025.
Wound care app can help determine appropriate wounddressings, posted date Apr. 24, 2013 [online], [retrieved Apr. 10, 2025]. Retrieved from internet, https://www.imedicalapps.com/2013/04/wound-care-app-dressings/. (Year: 2013).
PCT/US2021/065144 filed Dec. 23, 2021 International Search Report dated Oct. 4, 2022.
PCT/US2022/013569 filed Jan. 24, 2022 International Search Report and Written Opinion dated Aug. 29, 2022.
PCT/US2022/016020 filed Feb. 10, 2022 International Search Report and Written Opinion dated Oct. 31, 2022.
U.S. Appl. No. 17/848,074, filed Jun. 23, 2022 Advisory Action dated Jul. 9, 2024.
U.S. Appl. No. 17/848,074, filed Jun. 23, 2022 Final Office Action dated Apr. 26, 2024.
U.S. Appl. No. 17/848,074, filed Jun. 23, 2022 Non-Final Office Action dated Aug. 15, 2024.
U.S. Appl. No. 18/536,087, filed Dec. 11, 2023 Non-Final Office Action dated Jun. 28, 2024.
U.S. Appl. No. 18/536,087, filed Dec. 11, 2023 Notice of Allowance dated Aug. 29, 2024.
PCT/US2022/026999 filed Apr. 29, 2022 International Search Report and Written Opinion dated Oct. 24, 2022.
U.S. Appl. No. 17/589,849, filed Jan. 31, 2022 Notice of Allowance dated Aug. 23, 2023.
U.S. Appl. No. 17/848,074, filed Jun. 23, 2022 Non-Final Office Action dated Nov. 30, 2023.
PCT/US2022/031428 filed May 27, 2022 International Search Report and Written Opinion dated Jan. 30, 2023.
U.S. Appl. No. 17/547,128, filed Dec. 9, 2021 Non-Final Office Action dated Feb. 10, 2025.
U.S. Appl. No. 17/552,309, filed Dec. 15, 2021 Non-Final Office Action dated Mar. 14, 2025.
U.S. Appl. No. 17/552,309, filed Dec. 15, 2021 Restriction Requirement dated Dec. 12, 2024.
U.S. Appl. No. 17/583,090, filed Jan. 24, 2022 Non-Final Office Action dated Feb. 13, 2025.
U.S. Appl. No. 17/584,101, filed Jan. 25, 2022 Non-Final Office Action dated Feb. 5, 2025.
U.S. Appl. No. 17/678,965, filed Feb. 23, 2022 Non-Final Office Action dated Feb. 12, 2025.
U.S. Appl. No. 17/686,301, filed Mar. 3, 2022 Final Office Action dated Jan. 29, 2025.
U.S. Appl. No. 17/689,791, filed Mar. 8, 2022 Non-Final Office Action dated Dec. 30, 2024.
U.S. Appl. No. 17/690,908, filed Mar. 9, 2022 Non-Final Office Action dated Dec. 18, 2024.
U.S. Appl. No. 17/691,990, filed Mar. 10, 2022 Non-Final Office Action dated Dec. 17, 2024.
U.S. Appl. No. 17/694,416, filed Mar. 14, 2022 Non-Final Office Action dated Jan. 22, 2025.
U.S. Appl. No. 17/700,216, filed Mar. 21, 2022 Non-Final Office Action dated Feb. 5, 2025.
U.S. Appl. No. 17/709,019, filed Mar. 30, 2022 Non-Final Office Action dated Dec. 31, 2024.
U.S. Appl. No. 17/723,210, filed Apr. 18, 2022 Non-Final Office Action dated Dec. 20, 2024.
U.S. Appl. No. 17/849,419, filed Jun. 24, 2022 Final Office Action dated Feb. 14, 2025.
U.S. Appl. No. 17/857,997, filed Jul. 5, 2022 Restriction Requirement dated Feb. 12, 2025.
U.S. Appl. No. 17/859,995, filed Jul. 7, 2022 Non-Final Office Action dated Mar. 11, 2025.
U.S. Appl. No. 17/881,270, filed Aug. 4, 2022 Restriction Requirement dated Feb. 11, 2025.
Advantage Engineering, "Proper Use of Inhibited Propylene Glycol", Jun. 12, 2001, http://www.ttequip.com/knowledgelibrary/Proper%20Use%20Of%20Inh- ibited%20Propylene%20Glycol.pdf Jun. 12, 2001.
Hyperphysicis, "Thermal Conductivity", available Jul. 31, 2010, https://web.archive.org/web/20100731025127/http://hyperphysics.phy-astr.g- us.edu/hbase/tables.thron.html Jul. 31, 2010.
Murray, R. Z., et al. "Development and use of biomaterials as wound healing therapies" Burns & Trauma (2019) 7:2 https://doi.org/10.1186/s41038-018-0139-7 (2019).

(56) References Cited

OTHER PUBLICATIONS

P21TUS2022011971 filed Jan. 11, 2022 International Search Report and Written Opinion dated Apr. 21, 2022.
PCT/US2015/045548 filed Aug. 17, 2015 International Search Report and Written Opinion dated Nov. 24, 2015.
PCT/US2016/015688 filed Jan. 29, 2016 International Search Report and Written Opinion dated Apr. 1, 2016.
PCT/US2022/011980 filed Jan. 11, 2022 International Search Report and Written Opinion dated Apr. 13, 2022.
PCT/US2022/013007 filed Jan. 19, 2022 International Search Report and Written Opinion dated Apr. 22, 2022.
PCT/US2022/013672 filed Jan. 25, 2022, International Search Report and Written Opinion dated Jul. 15, 2022.
PCT/US2022/014147 filed Jan. 27, 2022 International Search Report and Written Opinion dated Jul. 18, 2022.
Sevgi, M., et. al. "Topical Antimicrobials for Burn Infections—An Update" Recent Pat Antiinfect Drug Discov. Dec. 2013 ; 8(3): 161-197.
Stoica, A. E., et al. "Hydrogel Dressings for the Treatment of Burn Wounds: An Up-To-Date Overview" Materials 2020, 13, 2853; doi:10.3390/ma13122853. (2020).
U.S. Appl. No. 15/512,025, filed Mar. 16, 2017 Final Office Action dated Jun. 25, 2020.
U.S. Appl. No. 15/512,025, filed Mar. 16, 2017 Non-Final Office Action dated Jul. 18, 2019.
U.S. Appl. No. 16/597,393, filed Oct. 9, 2019 Corrected Notice of Allowability dated Nov. 18, 2021.
U.S. Appl. No. 16/597,393, filed Oct. 9, 2019 Non-Final Office Action dated Apr. 28, 2021.
U.S. Appl. No. 17/589,849, filed Jan. 31, 2022 Final Office Action dated Jun. 27, 2023.
U.S. Appl. No. 17/589,849, filed Jan. 31, 2022 Non-Final Office Action dated Apr. 12, 2023.
Lustig et al. "Solute Diffusion in Swollen Membranes. IX. Scaling Laws for Solute Diffusion in Gels", Journal of Applied Polymer Science, vol. 36, pp. 735-747 (Year: 1988).
U.S. Appl. No. 17/547,128, filed Dec. 9, 2021 Advisory Action dated Nov. 19, 2025.
U.S. Appl. No. 17/547,128, filed Dec. 9, 2021 Final Office Action dated Aug. 27, 2025.
U.S. Appl. No. 17/547,128, filed Dec. 9, 2021 Non-Final Office Action dated Dec. 29, 2025.
U.S. Appl. No. 17/552,309, filed Dec. 15, 2021 Advisory Action dated Oct. 2, 2025.
U.S. Appl. No. 17/552,309, filed Dec. 15, 2021 Final Office Action dated Jul. 30, 2025.
U.S. Appl. No. 17/552,309, filed Dec. 15, 2021 Non-Final Office Action dated Nov. 5, 2025.
U.S. Appl. No. 17/583,090, filed Jan. 24, 2022 Notice of Allowance dated Sep. 30, 2025.
U.S. Appl. No. 17/584,101, filed Jan. 25, 2022 Final Office Action dated Oct. 23, 2025.
U.S. Appl. No. 17/686,301, filed Mar. 3, 2022 Final Office Action dated Oct. 28, 2025.
U.S. Appl. No. 17/689,791, filed Mar. 8, 2022 Advisory Action dated Jul. 24, 2025.
U.S. Appl. No. 17/689,791, filed Mar. 8, 2022 Non-Final Office Action dated Nov. 5, 2025.
U.S. Appl. No. 17/690,908, filed Mar. 9, 2022 Advisory Action dated Sep. 3, 2025.
U.S. Appl. No. 17/690,908, filed Mar. 9, 2022 Non-Final Office Action dated Oct. 2, 2025.
U.S. Appl. No. 17/691,990, filed Mar. 10, 2022 Advisory Action dated Jul. 24, 2025.
U.S. Appl. No. 17/691,990, filed Mar. 10, 2022 Non-Final Office Action dated Aug. 28, 2025.
U.S. Appl. No. 17/694,416, filed Mar. 14, 2022 Advisory Action dated Aug. 20, 2025.
U.S. Appl. No. 17/694,416, filed Mar. 14, 2022 Non-Final Office Action dated Oct. 1, 2025.
U.S. Appl. No. 17/697,879, filed Mar. 17, 2022 Non-Final Office Action dated Sep. 30, 2025.
U.S. Appl. No. 17/700,216, filed Mar. 21, 2022 Advisory Action dated Oct. 9, 2025.
U.S. Appl. No. 17/700,216, filed Mar. 21, 2022 Non-Final Office Action dated Dec. 3, 2025.
U.S. Appl. No. 17/709,019, filed Mar. 30, 2022 Advisory Action dated Jul. 24, 2025.
U.S. Appl. No. 17/709,019, filed Mar. 30, 2022 Non-Final Office Action dated Nov. 19, 2025.
U.S. Appl. No. 17/723,210, filed Apr. 18, 2022 Advisory Action dated Jul. 31, 2025.
U.S. Appl. No. 17/723,210, filed Apr. 18, 2022 Non-Final Office Action dated Dec. 29, 2025.
U.S. Appl. No. 17/837,956, filed Jun. 10, 2022 Non-Final Office Action dated Nov. 3, 2025.
U.S. Appl. No. 17/848,039, filed Jun. 23, 2021 Non-Final Office Action dated Jul. 29, 2025.
U.S. Appl. No. 17/848,039, filed Jun. 23, 2022 Final Office Action dated Dec. 29, 2025.
U.S. Appl. No. 17/857,997, filed Jul. 5, 2022 Final Office Action dated Oct. 27, 2025.
U.S. Appl. No. 17/859,995, filed Jul. 7, 2022 Advisory Action dated Oct. 28, 2025.
U.S. Appl. No. 17/859,995, filed Jul. 7, 2022 Final Office Action dated Aug. 22, 2025.
U.S. Appl. No. 17/859,995, filed Jul. 7, 2022 Non-Final Office Action dated Dec. 23, 2025.
U.S. Appl. No. 17/881,270, filed Aug. 4, 2022 Final Office Action dated Oct. 27, 2025.
U.S. Appl. No. 18/085,566, filed Dec. 20, 2022 Non-Final Office Action dated Oct. 1, 2025.
U.S. Appl. No. 18/272,026, filed Jul. 12, 2023 Non-Final Office Action dated Jul. 31, 2025.
U.S. Appl. No. 18/273,163, filed Jul. 19, 2023 Restriction Requirement dated Nov. 6, 2025.
U.S. Appl. No. 18/274,436, filed Jul. 26, 2023 Non-Final Office Action dated Oct. 1, 2025.
U.S. Appl. No. 18/289,341, filed Nov. 2, 2023 Restriction Requirement dated Nov. 6, 2025.
U.S. Appl. No. 19/068,969, filed Mar. 3, 2025 Non-Final Office Action dated Dec. 29, 2025.
U.S. Appl. No. 29/939,277, filed Apr. 25, 2024 Restriction Requirement dated Oct. 2, 2025.
U.S. Appl. No. 17/547,128, filed Dec. 9, 2021 Final Office Action dated Apr. 6, 2026.
U.S. Appl. No. 17/686,301, filed Mar. 3, 2022 Non-Final Office Action dated Apr. 3, 2026.
U.S. Appl. No. 17/691,990, filed Mar. 10, 2022 Final Office Action dated Mar. 9, 2026.
U.S. Appl. No. 17/694,416, filed Mar. 14, 2022 Final Office Action dated Apr. 9, 2026.
U.S. Appl. No. 17/697,879, filed Mar. 17, 2022 Non-Final Office Action dated Mar. 26, 2026.
U.S. Appl. No. 17/837,956, filed Jun. 10, 2022 Final Office Action dated Feb. 24, 2026.
U.S. Appl. No. 17/848,039, filed Jun. 23, 2022 Notice of Allowance dated Apr. 13, 2026.
U.S. Appl. No. 17/849,419, filed Jun. 24, 2022 Notice of Allowance dated Jan. 29, 2026.
U.S. Appl. No. 18/085,566, filed Dec. 20, 2022 Final Office Action dated Mar. 9, 2026.
U.S. Appl. No. 18/272,026, filed Jul. 12, 2023 Notice of Allowance dated Mar. 27, 2026.
U.S. Appl. No. 18/272,332, filed Jul. 13, 2023 Non-Final Office Action dated Mar. 25, 2026.
U.S. Appl. No. 18/272,332, filed Jul. 13, 2023 Restriction Requirement dated Jan. 21, 2026.
U.S. Appl. No. 18/273,163, filed Jul. 19, 2023 Non-Final Office Action dated Feb. 3, 2026.
U.S. Appl. No. 18/274,436, filed Jul. 26, 2023 Final Office Action dated Mar. 25, 2026.

(56) References Cited

OTHER PUBLICATIONS

U.S. Appl. No. 18/289,341, filed Nov. 2, 2023 Non-Final Office Action dated Feb. 18, 2026.
U.S. Appl. No. 18/715,504, filed May 31, 2024 Non-Final Office Action dated Apr. 9, 2026.
U.S. Appl. No. 18/715,504, filed May 31, 2024 Restriction Requirement dated Feb. 4, 2026.
U.S. Appl. No. 29/939,277, filed Apr. 25, 2024 Ex Parte Quayle Action dated Feb. 23, 2026.
U.S. Appl. No. 17/552,309, filed Dec. 15, 2021 Final Office Action dated Apr. 22, 2026.
U.S. Appl. No. 17/584,101 filed Jan. 25, 2022 Non-Final Office Action dated May 14, 2026.
U.S. Appl. No. 17/689,791, filed Mar. 8, 2022 Final Office Action dated Apr. 22, 2026.
U.S. Appl. No. 17/690,908, filed Mar. 9, 2022 Final Office Action dated May 12, 2026.
U.S. Appl. No. 17/691,990, filed Mar. 10, 2022 Advisory Action dated May 27, 2026.
U.S. Appl. No. 17/691,990, filed Mar. 10, 2022 Non-Final Office Action dated Jun. 29, 2026.
U.S. Appl. No. 17/694,416, filed Mar. 14, 2022 Advisory Action dated Jun. 16, 2026.
U.S. Appl. No. 17/700,216, filed Mar. 21, 2022 Final Office Action dated Jun. 24, 2026.
U.S. Appl. No. 17/709,019, filed Mar. 30, 2022 Final Office Action dated Apr. 22, 2026.
U.S. Appl. No. 17/723,210, filed Apr. 18, 2022 Final Office Action dated May 5, 2026.
U.S. Appl. No. 17/837,956, filed Jun. 10, 2022 Notice of Allowance dated May 7, 2026.
U.S. Appl. No. 17/859,995, filed Jul. 7, 2022 Advisory Action dated Jul. 2, 2026.
U.S. Appl. No. 17/859,995, filed Jul. 7, 2022 Final Office Action dated Apr. 28, 2026.
U.S. Appl. No. 18/085,566, filed Dec. 20, 2022 Advisory Action dated May 14, 2026.
U.S. Appl. No. 18/085,566, filed Dec. 20, 2022 Notice of Allowance dated Jun. 17, 2026.
U.S. Appl. No. 18/274,436, filed Jul. 26, 2023 Notice of Allowance dated Jun. 10, 2026.
U.S. Appl. No. 18/832,782, filed Jul. 24, 2024 Non-Final Office Action dated Apr. 20, 2026.
U.S. Appl. No. 18/837,098, filed Aug. 8, 2024 Non-Final Office Action dated Apr. 22, 2026.
U.S. Appl. No. 18/866,907, filed Nov. 18, 2024 Non-Final Office Action dated Jun. 29, 2026.
U.S. Appl. No. 19/018,774, filed Jan. 13, 2025 Non-Final Office Action dated Jun. 18, 2026.
U.S. Appl. No. 19/068,969, filed Mar. 3, 2025 Non-Final Office Action dated Apr. 28, 2026.
U.S. Appl. No. 29/939,277, filed Apr. 25, 2024 Notice of Allowance dated Jun. 10, 2026.

* cited by examiner

FIG. 6A
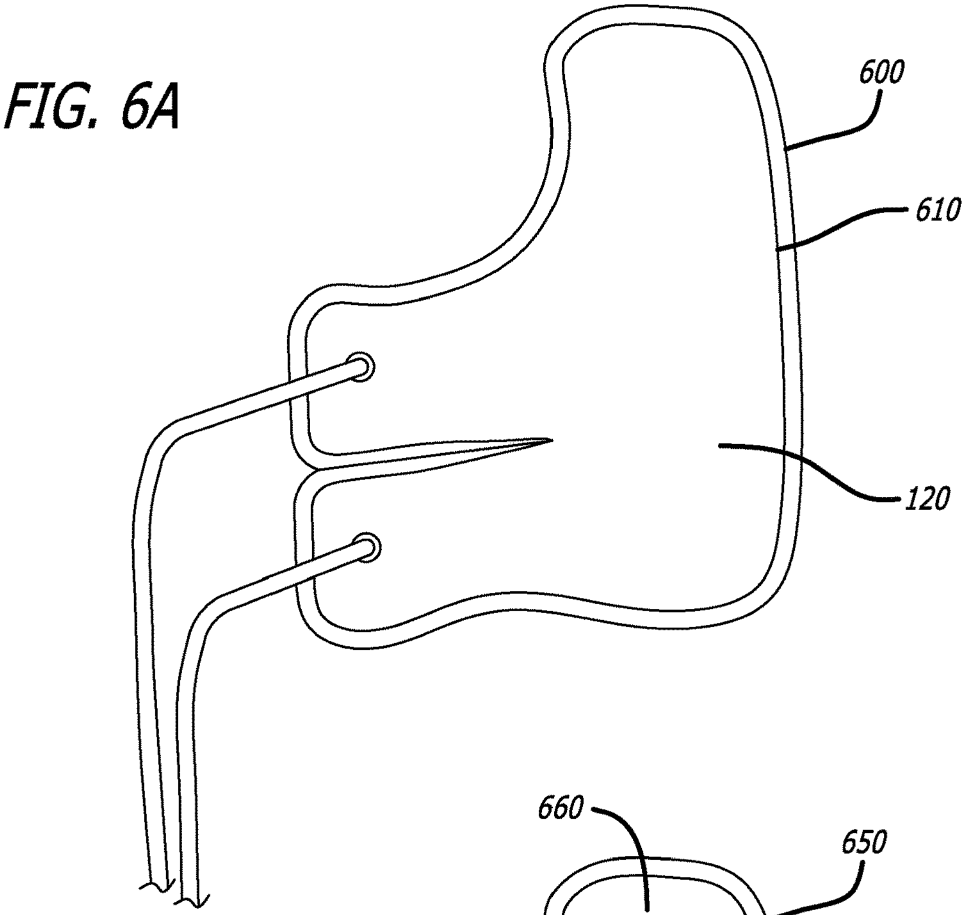
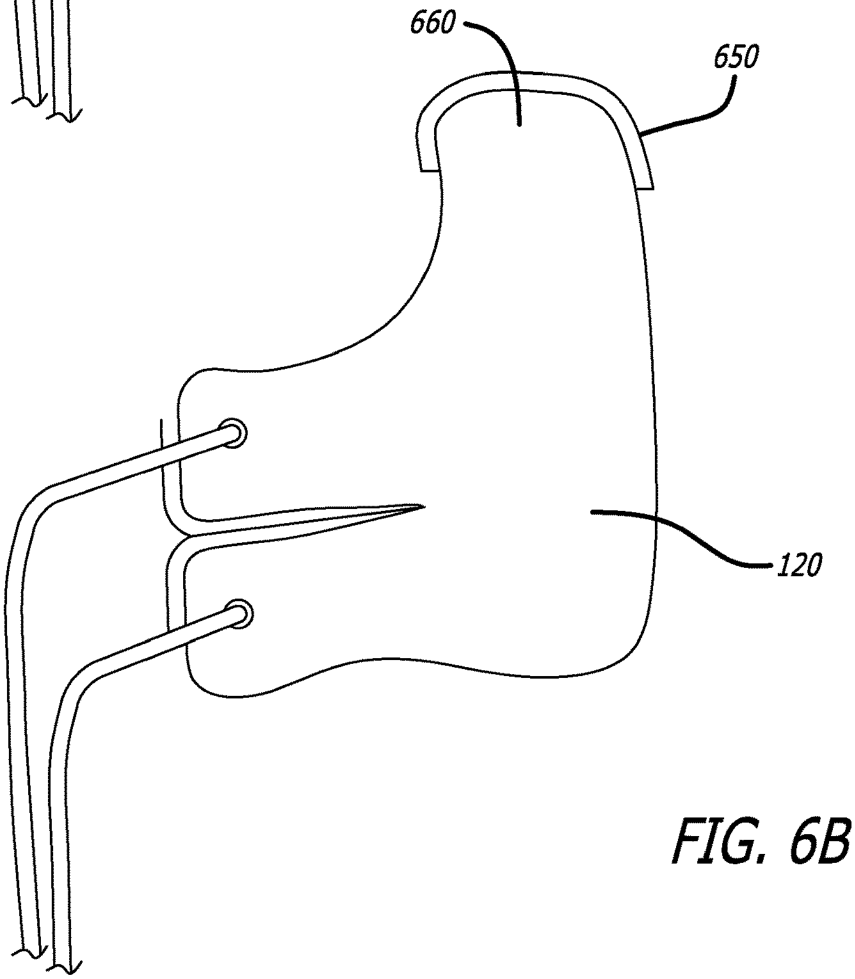
FIG. 6B

FIG. 7
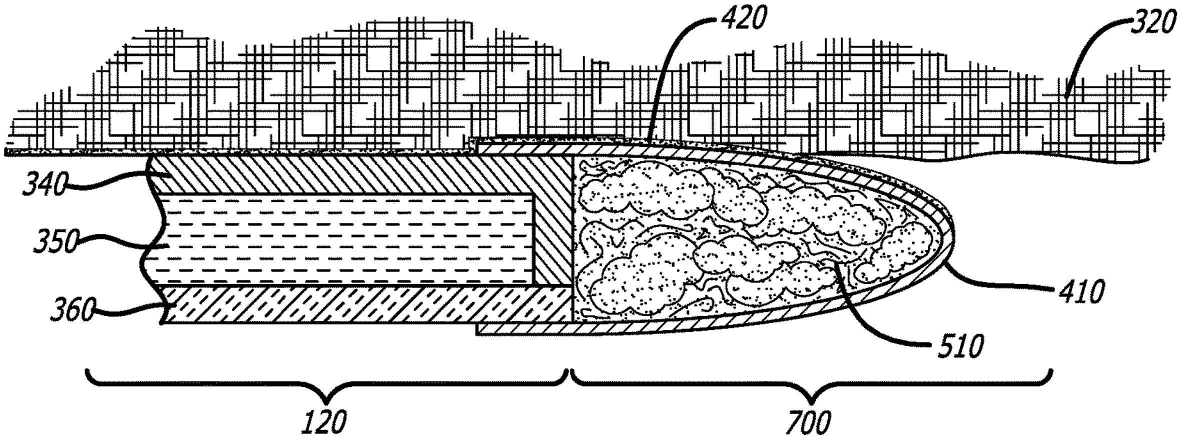
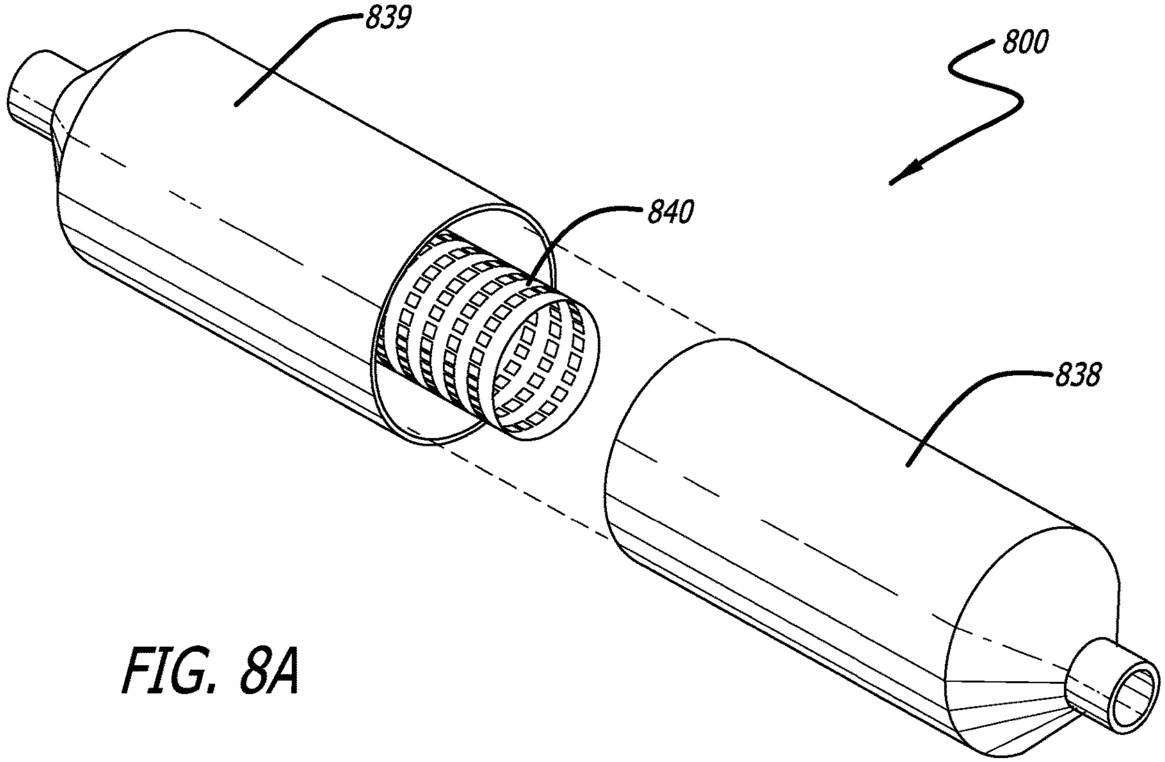
FIG. 8A

COOLING/HEATING MEDICAL PAD WITH SOFTENED EDGES

PRIORITY

This application is a U.S. national stage application of International Application No. PCT/US2022/013672, filed Jan. 25, 2022, which claims the benefit of priority to U.S. Provisional Application No. 63/141,294, filed Jan. 25, 2021, each of which is incorporated by reference in its entirety into this application.

SUMMARY

Briefly summarized, embodiments disclosed herein are directed to systems, methods and apparatuses for providing for a patient's comfort while undergoing Targeted Temperature Management (TTM), that is, cooling or heating a patient to provide medical benefits, such as neuroprotection following a stroke or surgery.

One problem that often arises with TTM systems is irritation of patients' skin due to pressure from an edge of the cooling and heating medical pads of the TTM system. Specifically, the medical pads may have a harsh edge, for example at curves or bends of the pads, that may cause discomfort and irritation for some patients. Even though the pads can contain a pliable material, like a hydrogel, that can conform to the patient's skin and provide good thermal contact, some patients may still experience skin irritation. In some cases, patients may use the pads for extended periods, exacerbating such discomfort and irritation after repeated contact. Embodiments of the disclosed apparatus and system can address this problem.

Disclosed herein is a medical pad for exchanging thermal energy with a patient. The medical pad can comprise a flexible upper sheet, a flexible base member, an edge guard, and an adhesive surface. The flexible base member is interconnected to the flexible upper sheet to define a fluid containing layer between the flexible base member and the flexible upper sheet. The edge guard is situated along an edge of the flexible upper sheet, and extends outwardly from the edge of the flexible upper sheet. The adhesive surface is disposed on a skin-contacting side of the flexible upper sheet and the edge guard. The adhesive surface is adapted for releasable adhesive contact with skin of the patient.

In some embodiments, the edge guard includes a pliant cover including a top cover portion and a bottom cover portion and a cushion filling. The adhesive surface is disposed along the top cover portion. The cushion filling is contained within the pliant cover and is configured to reduce pressure from the edge of the flexible upper sheet on the skin of the patient.

In some embodiments, the cushion filling of the edge guard comprises a thermally conductive material configured to conduct thermal energy between the fluid containing layer and the patient.

In some embodiments, the edge guard is configured to conform to a contour of the skin of the patient, so as to provide a direct path for the edge guard to conduct the thermal energy.

In some embodiments, the cushion filling comprises one or more of gauze filling, foam filling, or mesh filling.

In some embodiments, the pliant cover comprises one or more of woven fabric, polyvinyl chloride (PVC), polyethylene, polyurethane, another plastic, or latex.

In some embodiments, the edge guard is situated along the edge. The edge substantially surrounds a perimeter of the flexible upper sheet. The edge guard substantially surrounds the perimeter of the flexible upper sheet.

In some embodiments, the medical pad further comprises a conformable, thermally conductive layer of a hydrogel material.

In some embodiments, the flexible base member includes a plurality of dimples defining a plurality of tortuous fluid flow paths.

In some embodiments, the plurality of dimples are of a predetermined configuration comprising one or more of: a truncated cone configuration, a cylindrical configuration, or an elongated, truncated pyramid configuration.

In some embodiments, the plurality of dimples are arranged in a predetermined staggered pattern on an upper surface of the flexible base member, a lower smooth surface of the flexible upper sheet is supported at a plurality of points of contact with the dimples, and the dimples are staggered in at least two transverse directions on the upper surface of the flexible base member.

In some embodiments, the predetermined staggered pattern comprises offset rows and columns.

In some embodiments, the dimples within adjacent rows and adjacent columns are offset from one another by sixty degrees.

In some embodiments, the dimples are arranged in a herringbone pattern.

In some embodiments, the base member is formed to integrally define the plurality of dimples.

In some embodiments, a filter is disposed in line with a fluid flow path providing a fluid to the medical pad. In some embodiments, the filter comprises a porous wall disposed parallel to a flow direction of the fluid along the fluid flow path. In some embodiments, the filter is attached to the medical pad. In some embodiments, the filter is disposed within the fluid containing layer of the medical pad.

Also disclosed herein is a medical pad for exchanging thermal energy with a patient. The medical pad can comprise a flexible base member, a flexible film, a thermally conductive layer, an edge guard, and an adhesive surface. The flexible base member is of foam construction and has a plurality of integrally defined dimples. The flexible film is interconnected to the flexible base member to define a fluid containing layer between the flexible base member and the flexible film. The plurality of dimples define tortuous fluid flow paths within the fluid containing layer. The thermally conductive layer is laminated to one side of the flexible film. The edge guard is situated along an edge of the thermally conductive layer, wherein the edge guard extends outwardly from the edge of the thermally conductive layer. The adhesive surface is disposed on the thermally conductive layer and the edge guard. The adhesive surface is adapted for releasable adhesive contact with skin of a patient.

Also disclosed herein is a medical pad for contacting and exchanging thermal energy with a patient. The medical pad can comprise a fluid containing layer, a fluid inlet, a fluid outlet, an adhesive surface, and an edge guard. The fluid containing layer contains a thermal exchange fluid configured to exchange thermal energy with the patient. The thermal exchange fluid transfers thermal energy to the patient while circulating within the fluid containing layer from the fluid inlet to the fluid outlet. The adhesive surface is disposed on a skin contacting side of the fluid containing layer, wherein thermal energy is exchangeable across the adhesive surface. The edge guard is situated along an edge of the adhesive surface between the adhesive surface and the patient.

These and other features of the concepts provided herein will become more apparent to those of skill in the art in view of the accompanying drawings and following description, which disclose particular embodiments of such concepts in greater detail.

BRIEF DESCRIPTION OF THE DRAWINGS

Embodiments of the disclosure are illustrated by way of example and not by way of limitation in the figures of the accompanying drawings, in which like references indicate similar elements and in which:

FIG. 6A illustrates an edge guard surrounding the perimeter of a medical pad, according to some embodiments;

FIG. 6B illustrates an edge guard covering a portion of the perimeter of a medical pad, according to some embodiments;

FIG. 7 illustrates details of an alternative embodiment of an edge guard, according to some embodiments;

FIG. 8A provides an exploded perspective view of a TTM fluid filter, according to some embodiments;

DETAILED DESCRIPTION

Figure 1:
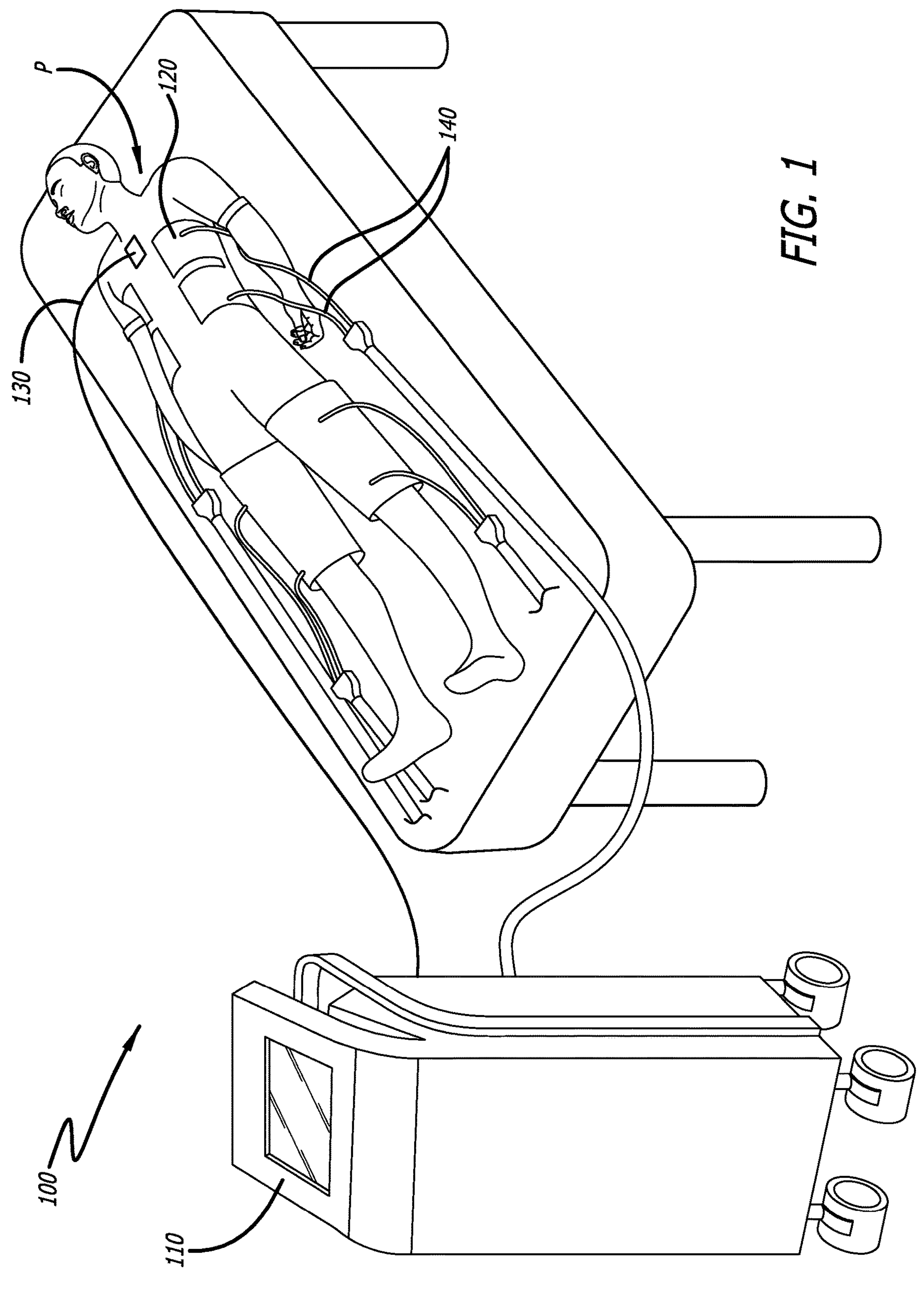
FIG. 1 illustrates a targeted temperature management (TTM) system using medical pads for heating and/or cooling a patient, according to some embodiments.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal end portion" of, for example, a probe disclosed herein includes a portion of the probe intended to be near a clinician when the probe is used on a patient. Likewise, a "proximal length" of, for example, the probe includes a length of the probe intended to be near the clinician when the probe is used on the patient. A "proximal end" of, for example, the probe includes an end of the probe intended to be near the clinician when the probe is used on the patient. The proximal portion, the proximal end portion, or the proximal length of the probe can include the proximal end of the probe; however, the proximal portion, the proximal end portion, or the proximal length of the probe need not include the proximal end of the probe. That is, unless context suggests otherwise, the proximal portion, the proximal end portion, or the proximal length of the probe is not a terminal portion or terminal length of the probe.

With respect to "distal," a "distal portion" or a "distal end portion" of, for example, a probe disclosed herein includes a portion of the probe intended to be near or in a patient when the probe is used on the patient. Likewise, a "distal length" of, for example, the probe includes a length of the probe intended to be near or in the patient when the probe is used on the patient. A "distal end" of, for example, the probe includes an end of the probe intended to be near or in the patient when the probe is used on the patient. The distal portion, the distal end portion, or the distal length of the probe can include the distal end of the probe; however, the distal portion, the distal end portion, or the distal length of the probe need not include the distal end of the probe. That is, unless context suggests otherwise, the distal portion, the distal end portion, or the distal length of the probe is not a terminal portion or terminal length of the probe.

The term "logic" may be representative of hardware, firmware or software that is configured to perform one or more functions. As hardware, the term logic may refer to or include circuitry having data processing and/or storage functionality. Examples of such circuitry may include, but are not limited or restricted to a hardware processor (e.g., microprocessor, one or more processor cores, a digital signal processor, a programmable gate array, a microcontroller, an application specific integrated circuit "ASIC", etc.), a semiconductor memory, or combinatorial elements.

Additionally, or in the alternative, the term logic may refer to or include software such as one or more processes, one or more instances, Application Programming Interface(s) (API), subroutine(s), function(s), applet(s), servlet(s), routine(s), source code, object code, shared library/dynamic link library (dll), or even one or more instructions. This software may be stored in any type of a suitable non-transitory storage medium, or transitory storage medium (e.g., electrical, optical, acoustical or other form of propagated signals such as carrier waves, infrared signals, or digital signals). Examples of a non-transitory storage medium may include, but are not limited or restricted to a programmable circuit; non-persistent storage such as volatile memory (e.g., any type of random access memory "RAM"); or persistent storage such as non-volatile memory (e.g., read-only memory "ROM", power-backed RAM, flash memory, phase-change memory, etc.), a solid-state drive, hard disk drive, an optical disc drive, or a portable memory device. As firmware, the logic may be stored in persistent storage.

The effect of temperature variations on the human body has been well documented. Elevated temperatures may be harmful to the brain under normal conditions, and even more importantly, during periods of physical stress, such as illness or surgery. Conversely, lower body temperatures, or mild hypothermia, may offer some degree of neuroprotection. Moderate to profound hypothermia (below 32° C.) tends to be more harmful to the body and may lead to death.

Targeted Temperature Management (TTM) refers to cooling or heating a patient to provide medical benefits, such as neuroprotection following a stroke or surgery. TTM or thermoregulation can be viewed in two different ways. The first aspect of temperature management includes treating abnormal body temperatures, i.e. cooling the body from elevated temperatures (hyperthermia), or warming the body to manage hypothermia. Hypothermia may occur in response to exposure to cold environments, trauma, or long complex surgical procedures. Hyperthermia may occur in response to systemic inflammation, sepsis, stroke, or other brain injury.

The second aspect of thermoregulation is a treatment that employs techniques that physically control a patient's temperature to provide a physiological benefit, such as cooling for a degree of neuroprotection. Studies have shown that treatment with mild hypothermia, defined as lowering core body temperature 2-3° C., confers neuroprotection in stroke victims, and may hasten neurologic recovery and improve outcomes when applied for 24 to 72 hours in cases of traumatic brain injury. In particular, research suggests that brain damage from a stroke may take hours to reach maximum effect. Neurologic damage may be limited and the stroke victim's outcome improved if a neuroprotectant therapy, such as cooling, is applied within this time frame.

A TTM system using medical pads can regulate body temperature for patients who undergo procedures requiring therapeutic TTM and/or to assist in controlling temperature for specific medical or surgical conditions. Such a system is described in U.S. Pat. No. 6,645,232, titled "Patient Temperature Control System with Fluid Pressure Maintenance," and the medical pads are described in U.S. Pat. No. 6,375,674, titled "Cooling/Heating Pad and System," each of which is incorporated herein by reference in its entirety into this application.

One problem that often arises with TTM systems is irritation of patients' skin due to pressure from an edge of the cooling and heating medical pads of the TTM system. Specifically, the medical pads may have a harsh edge, for example at curves or corners, that may cause discomfort and irritation for some patients. Even though the pads can contain an adaptable material, like a hydrogel, that can conform to the patient's skin and provide good thermal contact, some patients may still experience skin irritation. In some cases, patients may use the pads for extended periods, exacerbating such discomfort and irritation after repeated contact. Embodiments of the disclosed apparatus and system can address this problem.

Reference is now made to FIG. 1, which illustrates a TTM system 100 using medical pads 120 for heating and/or cooling a patient P, according to some embodiments. The illustrated patient temperature control system 100 is a thermoregulatory system and apparatus that monitors and controls patient temperature within a range of 32° C. to 38.5° C. (89.6° F. to 101.3° F.). TTM system 100 is selectively interconnected to one or more medical contact pads 120 for exchanging thermal energy with patient P, and can also include a circulating pump for drawing temperature-controlled thermal fluid (e.g., water or a gas) through pads 120 under negative pressure.

In some embodiments, TTM system 100 can include a control module 110, one or more disposable medical contact pads 120 (pads or medical pads) configured to facilitate thermal energy exchange with a fluid and the patient P, a remote display in control module 110, a patient temperature probe 130, one or more fluid circulation lines 140, and any additional accessories. In a typical embodiment, there may be two pads 120 placed on the patient's upper body as shown, and two on the patient's lower body (not shown). The TTM system 100 may use negative pressure to draw temperature-controlled fluid, such as water ranging between 4° C. and 42° C. (39.2° F. and 107.6° F.), through the pads 120 at approximately 0.7 liters per minute per pad. This results in heat exchange between the circulating fluid and the patient P. The patient temperature probe 130 is connected to the control module 110, and provides patient temperature feedback information to an internal control algorithm of control module 110. Based on such an internal control algorithm, control module 110 can increase or decrease the circulating water temperature so as to heat or cool patient P to a target patient temperature, which can be set by the clinician.

Fluid circulation lines 140 (or "fluid delivery lines") may include opposing tubing assemblies for interconnection to outlet and inlet ports of the circulating pump, with pads 120 fluidly interconnectable by means of opposing pad manifolds. FIG. 1 also illustrates the interconnection of one or more external or internal patient temperature sensors 130 with a signal conditioning interface of control module 110. The temperature information received from temperature sensors 130 may be utilized at a processor of control module 110 to determine the amount and rate of thermal exchange to be affected by system 100 in relation to the preset or user-defined patient target temperature. Accordingly, the processor may provide appropriate control drive signals to a heater, radiator, fan and/or auxiliary pump of TTM system 100. In an embodiment, the circulating pump, heater, radiator, fan, and/or auxiliary pump may be housed within control module 110.

Figure 2:
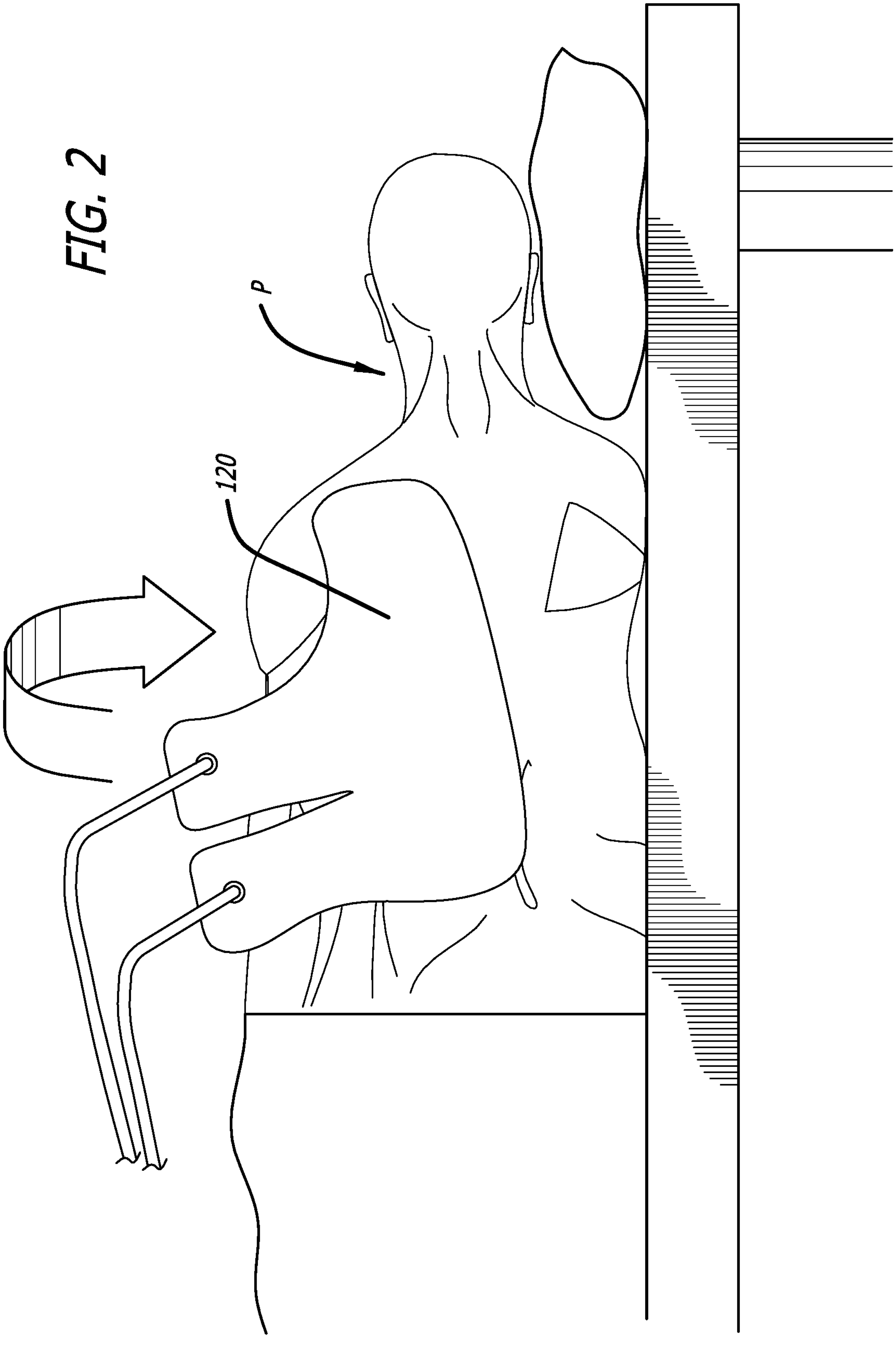
FIG. 2 illustrates pads being placed on a patient, according to some embodiments.

FIG. 2 illustrates a pad 120 being placed on a patient P, according to some embodiments. Pad 120, and particularly an inner layer of pad 120 containing biocompatible hydrogel, can conform to the patient's skin, and thereby provide good thermal contact with patient P. The medical pad 120 can include several layers such as an inner biocompatible hydrogel layer that adheres and conforms to the patient P, a fluid containing layer, one or more thin film layers which serve as a fluid barrier, and an outer insulating layer which prevents heat transfer to the environment (see FIG. 3). The hydrogel layer can have sufficient adhesive strength to hold pads 120 in place on patient P during the TTM therapy, yet not cause tissue damage when subsequently removed.

The pads 120 may be available in extra-small, small, medium, and large sizes, as well as a universal pad, among others. The clinician can determine the style, size, and number of pads 120 to be applied to patient P based on the patient procedure, application, or the available body surface area on patient P. For example, the clinician may place two pads 120 on the patient's upper body, such as on the patient's back and torso as illustrated in FIG. 2, and two pads on the patient's lower body, for example wrapped around the patient's thighs. The pads 120 will provide the best performance when the maximum number and correct size are used.

In some embodiments, due to the negative fluid pressure applied by system 100, significant fluid leakage will not occur, even in the event pads 120 are damaged or broken while fluid is flowing. Accordingly, pads 120 can be applied to the patient while fluid is already flowing through the pads. Depending on the objective of the treatment and whether the patient is conscious (or otherwise awake and coherent), pads 120 may be pre-warmed or pre-cooled prior to placement.

In order to place the pad 120, a clinician will first align the top of a first upper body pad 120 with axilla of the patient's outstretched arm. The clinician will then place the long side of pad 120 along the side of the patient's spine. Next, the clinician can wrap pad 120 from back to front as illustrated, ensuring that the pad's fluid inlet and outlet lines are lying anteriorly. For the lower body, the clinician can align the first lower body pad's lines with the knee and point downward. The clinician will wrap the long end of the first lower body pad laterally, and overlap medially if needed.

The clinician may then turn the patient P and place a second upper body pad on the patient's other side, leaving a space along the patient's spine. Next, the clinician can wrap a second lower body pad around the patient's other leg, ensuring that the shorter edge is placed medially, and the longer side is wrapped laterally. Further, if additional surface coverage is needed, the clinician can optionally place a universal pad on the patient's abdomen.

The pads 120 have inlet and outlet lines for the fluid flow, referred to herein as pad lines. These lines are connected to the pads 120 by means of a pad manifold. In particular, a Y-shaped fluid delivery line contains one-way valves that connect to pad line connectors (e.g., a total of six connectors). Each side of the fluid delivery line can be placed by the patient's feet or along the patient's lower legs. The connectors can accommodate a full set of four pads 120 plus a maximum of two optional universal pads for larger patients. While holding the pad line tubing, the clinician can insert a pad line connector into the pad fluid delivery line manifold. For example, the clinician can push a respective connector toward the manifold to release associated catches, and then pull apart. Subsequently, the clinician can disconnect the lines, e.g., by squeezing wings on the connector together.

Figure 3:
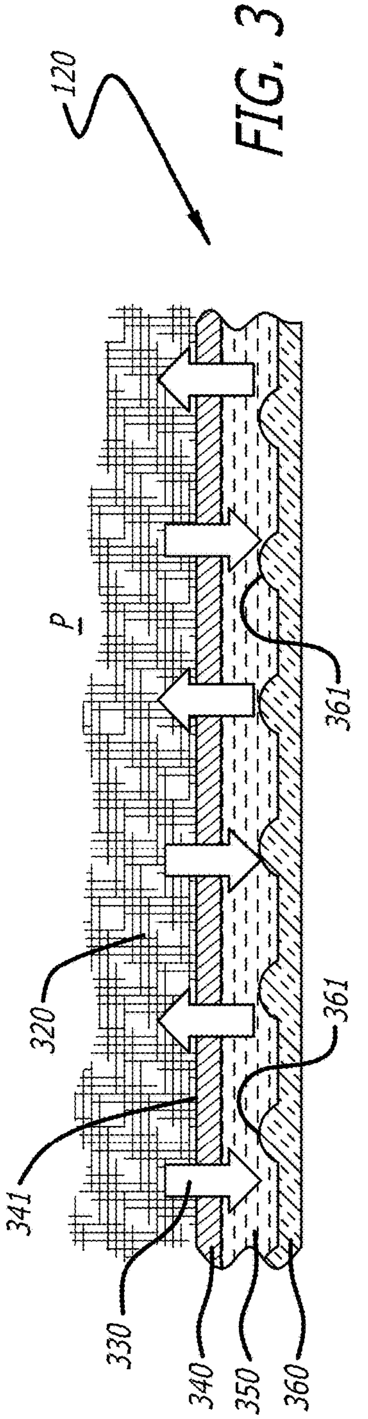
FIG. 3 illustrates a structure of an exemplary medical pad, according to some embodiments.

FIG. 3 illustrates a structure of an exemplary pad 120, according to some embodiments. The pad 120 comprises inner biocompatible hydrogel layer 340 (or "conformable thermal conduction layer"), which can adjoin and conform to patient's skin 320. Further, the pad 120 may include an adhesive layer 341 disposed on the skin contacting side of the hydrogel layer 340 for adhering the pad 120 to the patient's skin 320. While not shown, a removable release liner may be provider over the adhesive surface 341 to protect the adhesive surface 341 from contamination while the pad 120 is not in use.

Pad 120 additionally comprises fluid containing layer 350 and insulation layer 360 for preventing loss of thermal energy to the environment. The fluid containing layer 350 can be defined between one or more film layers and/or insulation layer 360. The fluid can be heated or cooled to a temperature between 4° C. and 42° C. (39.2° F. and 107.6° F.), and can circulate through fluid containing layer 350, exchanging thermal energy 330 with patient's skin 320 via hydrogel layer 340, so as to warm or cool patient P to the target temperature. Although in this example, heat energy 330 is shown flowing from skin 320 to the fluid in layer 350, heat 330 can flow in either direction between patient P and layer 350, so as to heat or cool patient P to the target temperature.

Alternatively, in some embodiments, pad 120 comprises hydrogel layer 340, a thin film layer which serves as a fluid barrier, and outer insulating layer 360 comprising foam with water channels.

A hydrogel is an appropriate material for layer 340 because the hydrogel is biocompatible, its adhesive strength does not tend to increase over time as compared with traditional adhesive, it tends to envelop hair on patient's skin 320, thereby facilitating good thermal contact, and its high water content results in relatively high thermal conductivity. Accordingly, hydrogel layer 340 may function as a thermally conductive layer, while also having sufficient adhesive properties so as to integrally provide an adhesive surface. Alternatively, in some embodiments, the conformable, thermally conductive layer and adhesive surface can be comprised of different materials. For example, an appropriate adhesive material may be sprayed or otherwise applied onto the surface of a layer of an appropriate conformable, thermally conductive material different than the adhesive material.

Fluid containing layer 350 can include tortuous fluid flow paths, which can be defined by dimples 361 or other elongated members on insulation layer 360 or within the fluid containing layer 350. Such tortuous fluid flow paths can serve to regulate the fluid flow, and to inhibit the formation of boundary layers wherein some of the fluid remains substantially stationary along the inside surfaces of the fluid containing layer 350. Such boundary layers could reduce the efficiency of the pad 120 because the stationary fluid remains within the fluid containing layer 350, but eventually becomes ineffective at heating or cooling patient P as it approaches the existing temperature of patient P. Furthermore, the crisscrossed geometry of elongated members defining the tortuous flow paths also facilitates an even, low pressure drop between the inlet and the outlet required by a negative flow pressure circulating system.

Even though pads 120 can contain a conformable, biocompatible material, like hydrogel layer 350, some patients may still experience skin irritation while using the pads 120. In some cases, discomfort and skin irritation may be caused by pressure from the edges of pads 120. Specifically, pads 120 may have a harsh or rough-textured edge, for example at corners or regions of curvature, that may cause discomfort and irritation for some patients. In some cases, patients may use the pads for extended periods, exacerbating such discomfort and irritation after repeated contact. The disclosed edge guard apparatus and system can address this problem.

Figure 4:
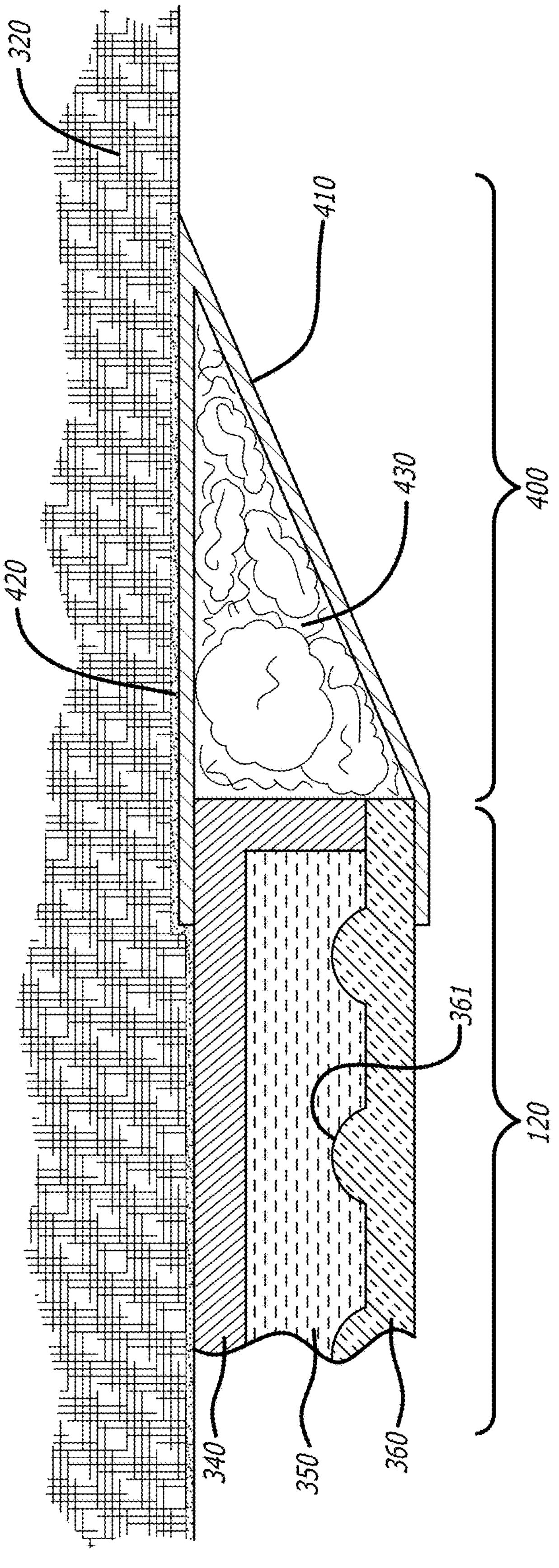
FIG. 4 illustrates a structure of a medical pad with an edge guard, according to some embodiments.

FIG. 4 illustrates a structure of a pad 120 with an edge guard 400, according to some embodiments. In order to reduce any irritation that may affect the patient's skin 320 when in contact with pad 120, the disclosed edge guard 400 may extend outwardly from the edge of pad 120, and serve as a flexible barrier between pad 120 and skin 320. In this example, edge guard 400 has a triangular solid shape, tapering from an initial thickness that covers all three layers 340, 350, and 360 of pad 120. Alternatively, edge guard 400 may have another shape or size, for example a rectangular solid of thickness that covers all three layers of pad 120, a rectangular solid covering only hydrogel layer 340, or a triangular solid tapering from an initial thickness of only hydrogel layer 340. Edge guard 400 can surround the edges of pad 120 and be filled with a soft, padded filling 430. This filling 430 serves to taper and soften any harsh corners and edges of the pad 120, thereby ameliorating the side effects of TTM treatment, i.e., patient discomfort and skin irritation.

As described in the example of FIG. 3 above, the medical pad 120 comprises a hydrogel layer 340, which can contact and conform to the patient's skin 320. Pad 120 additionally comprises film layer 350, which forms a base for fluid flow paths through pad 120, and insulation layer 360, which prevents loss of thermal energy to the environment.

Edge guard 400 can extend from the edges of pad 120. Edge guard 400 may comprise separate materials from pad 120, and may be attached or fastened to pad 120. In some embodiments, antiseptic material is used to fasten edge guard 400 to the edges of pad 120. Alternatively, the edge guard 400 may be formed from an extension or continuation of the same materials comprising the pad 120, and is not limited by the present disclosure.

In this example, edge guard 400 is covered by an elastic outer shell 410. In some embodiments, outer shell 410 comprises a material such as, e.g., woven fabric, plastic (such as polyvinyl chloride (PVC), polyethylene, or polyurethane), or latex. In various embodiments, outer shell 410 may be adhesive, or a separate adhesive layer 420 may cover outer shell 410, in order to adhere edge guard 400 to skin 320. In an example, adhesive layer 420 may cover pad 120, or the hydrogel layer 340 thereof, and may extend over edge guard 400, as well.

Figure 5A:
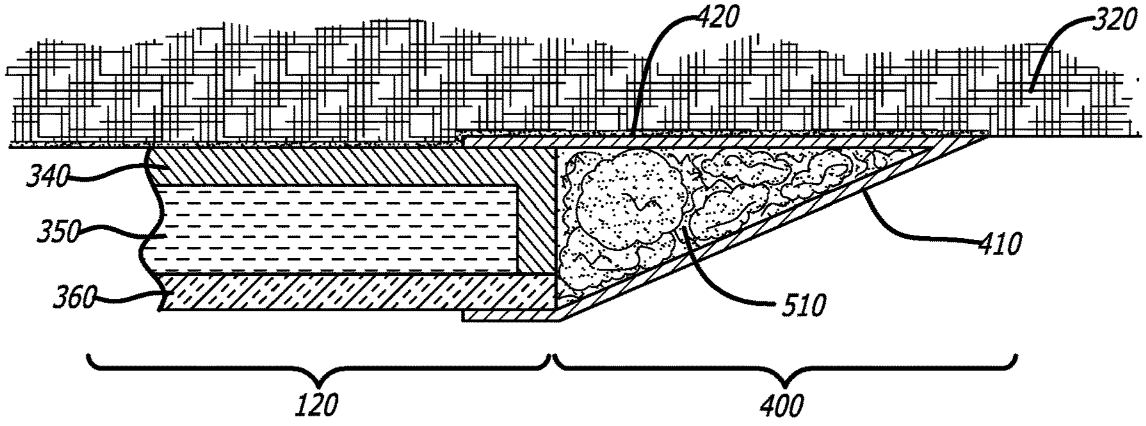
FIG. 5A illustrates a structure of an edge guard containing gauze, according to some embodiments.
Figure 5B:
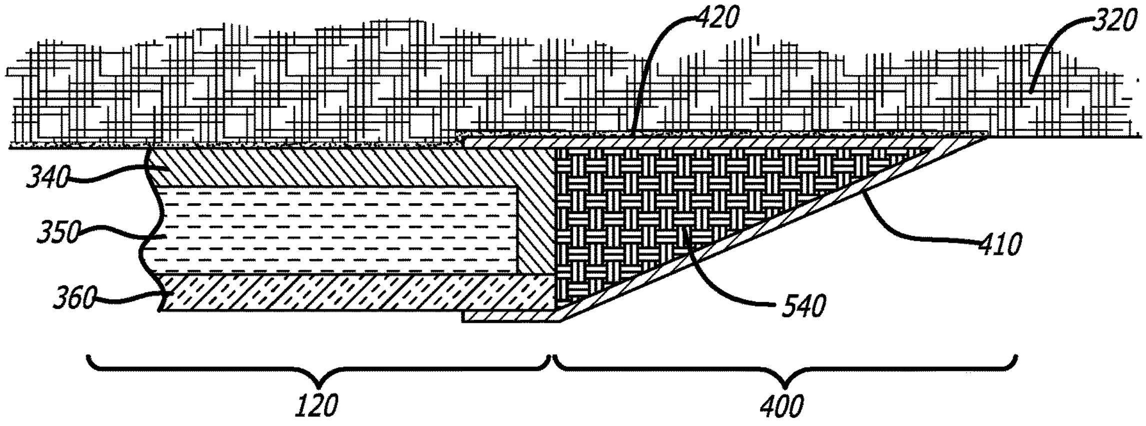
FIG. 5B illustrates a structure of an edge guard containing foam, according to some embodiments.
Figure 5C:
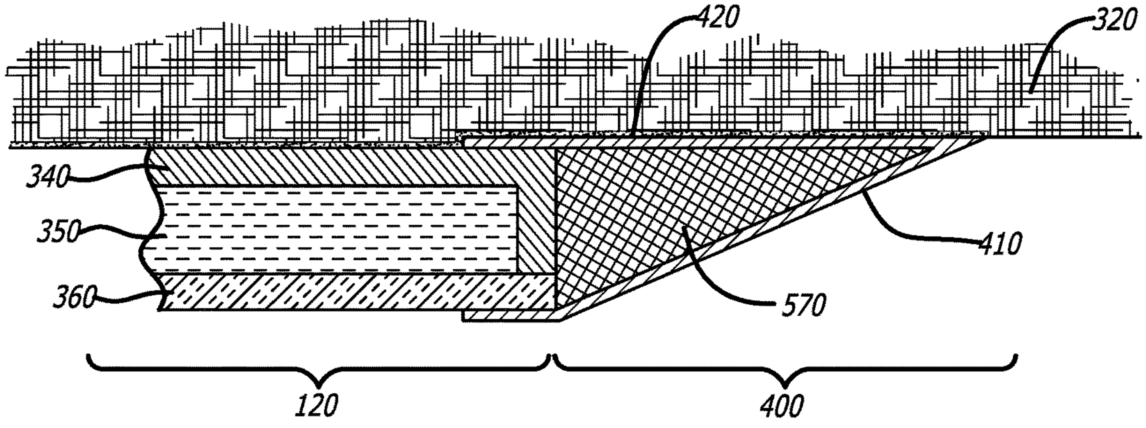
FIG. 5C illustrates a structure of an edge guard containing mesh, according to some embodiments.

Edge guard 400 can contain a soft filling 430, such as soft foam, cotton gauze, or mesh (see FIGS. 5A-5C). In some embodiments, filling 430 can comprise another material, such as polyester, wool, or latex. Filling 430 can absorb pressure from the edges of medical pad 120, and can thereby soften the impact of medical pad 120, and particularly its harsh edges, on the patient's skin 320. Accordingly, medical pad 120 can remain on the patient's skin 320 during the course of extended TTM treatments, e.g., for hours or days, without irritating skin 320 or causing significant discomfort to the patient. In some embodiments, filling 430 can include a thermally conductive material configured to conduct thermal energy between the pad 120 and the patient's skin 320.

In some embodiments, antiseptic material used to attach edge guard 400 to the edge of pad 120 can further reduce pressure from the pad 120 to skin 320.

Figure 8B:
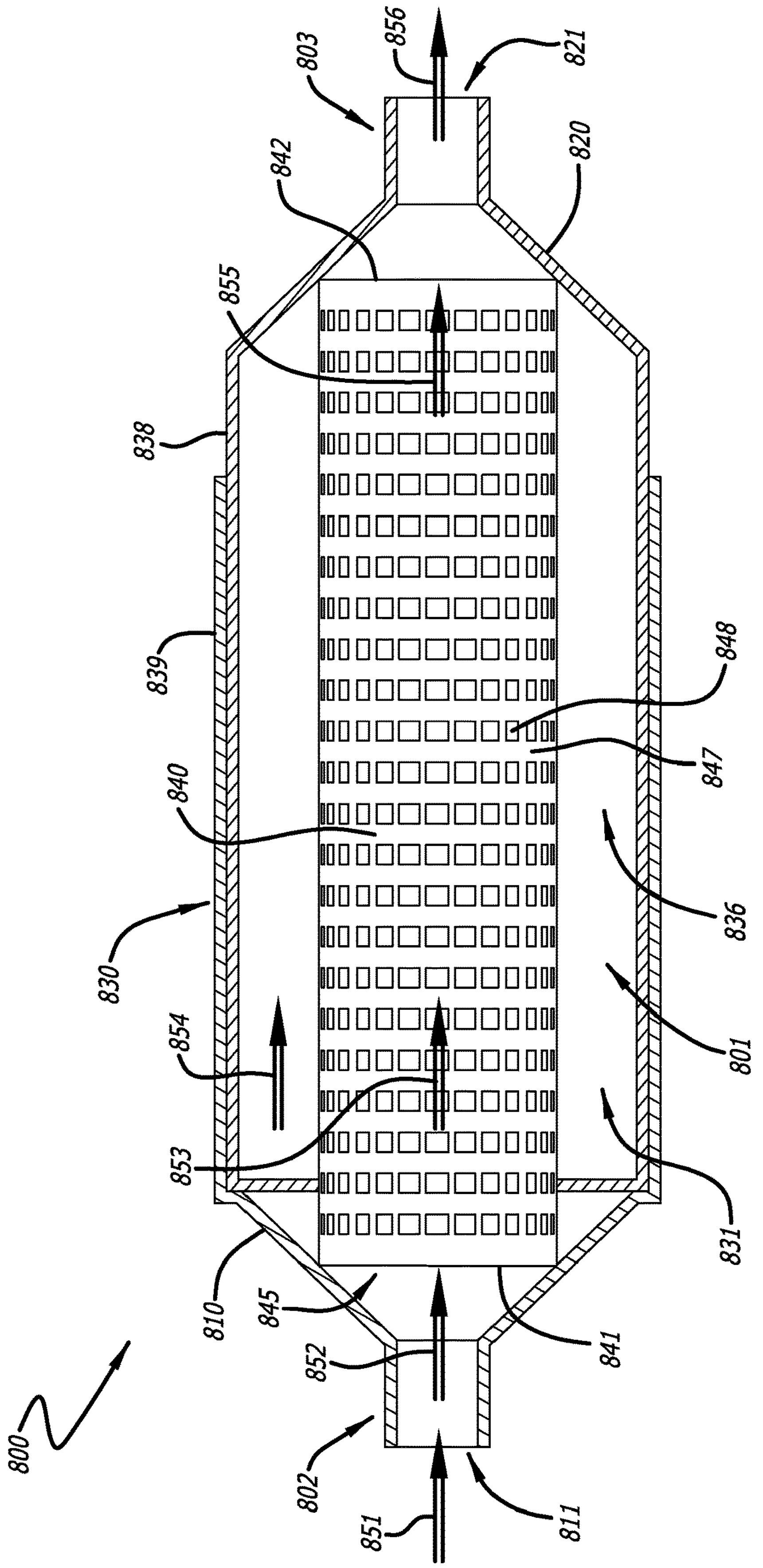
FIG. 8B provides a cross-sectional side view of the filter of FIG. 8A, according to some embodiments.
Figure 8C:
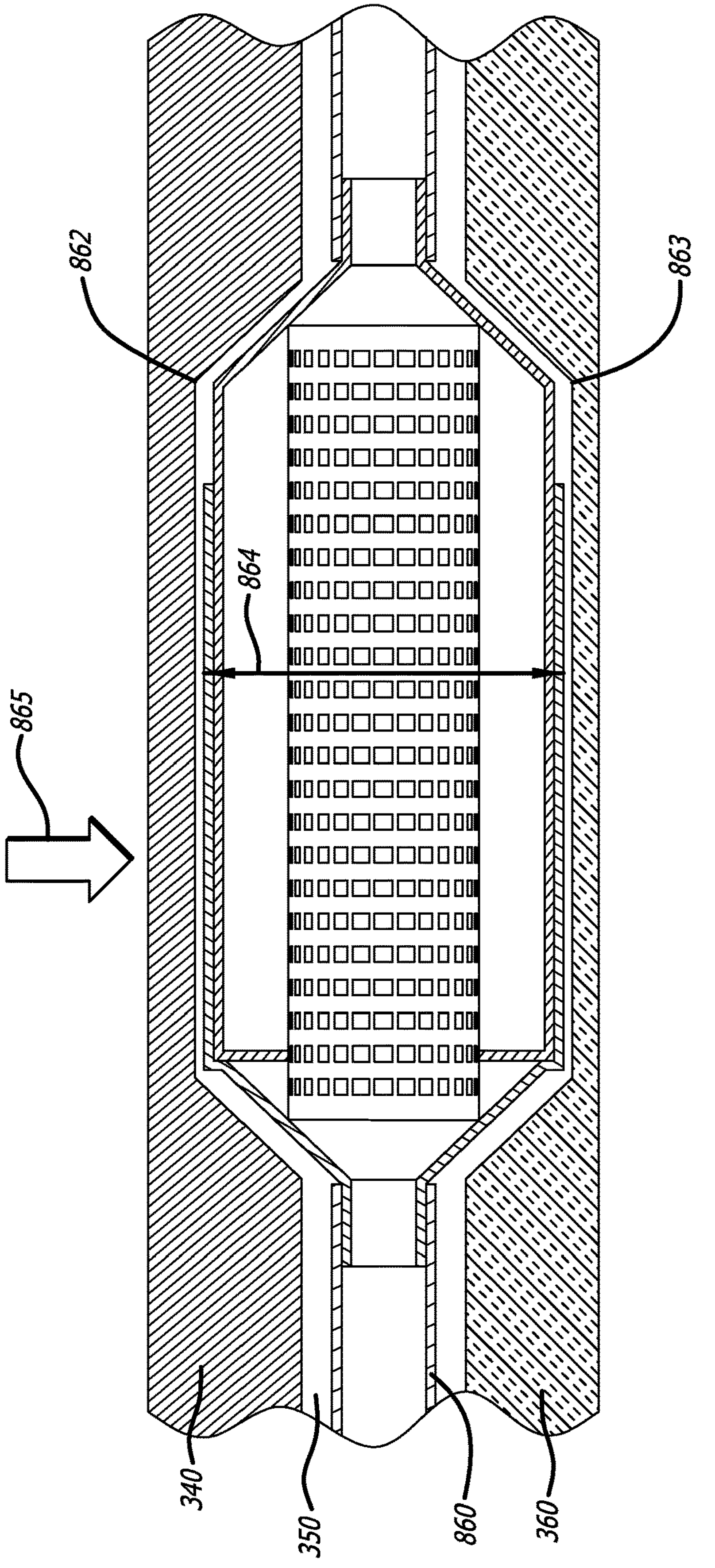
FIG. 8C provides a side cross-sectional view of a medical pad incorporating the filter of FIG. 8A, according to some embodiments.

In some embodiments, as noted above, the fluid containing layer 350 may include tortuous fluid flow paths. In some embodiments, the tortuous fluid flow paths may be comprised of tortuous tubing disposed within the fluid containing layer 350. For example, the tortuous tubing, which may be referred to as one or more interna flow paths, may include a filter, as seen in FIGS. 8A-8C.

FIG. 5A illustrates an exemplary structure of an edge guard 400 containing gauze 510, according to some embodiments. Pad 120 comprises hydrogel layer 340, which can adjoin and conform to patient's skin 320. Pad 120 additionally comprises fluid containing layer 350, which can include tortuous fluid flow paths and may be contained between one or more film layers, and insulation layer 360, which prevents loss of thermal energy to the environment. In this example, adhesive layer 420 covers pad 120 and extends over edge guard 400, as well.

As shown, edge guard 400 can extend outwardly from the edge of pad 120 and be attached thereto. Edge guard 400 is covered by outer shell 410, and contains gauze filling 510. For example, gauze 510 may comprise cotton, one or more gauze swabs or sponges, one or more gauze balls, silk, scrim, plastic porous film, a polyblend, and/or another gauze material. In some embodiments, the gauze may be formed into gauze balls, which may be contained within mesh.

Although edge guard 400 is illustrated as having a substantially triangular solid shape, outer shell 410 may be pliant or flexible, such that the shape of edge guard 400 may conform to the patient's skin 320, and/or may deform in response to pressure, including for extended periods of time. This may be especially true for the part of the outer shell 410 that faces away from the patient's skin 320 (i.e., the lower part as shown in FIG. 5A), which may curve and/or bend in response to forces and pressures. Of course, such mechanical responses by edge guard 400 to external forces, e.g., from pad 120, can reduce patient discomfort, since the forces could otherwise be transmitted to the patient's skin 320. Furthermore, in various embodiments, edge guard 400 may instead be formed in any other shape, such as a rectangular solid, an oblate spheroid (see FIG. 7), etc.

Because gauze 510 is very soft, it can absorb pressure or mechanical impacts from the edge of pad 120 and cushion the patient's skin, thereby increasing patient comfort and improving patient tolerance, even during an extended TTM treatment. Moreover, edge guard 400 containing gauze 510 can function as a barrier between the edge of pad 120 and the patient's skin. That is, edge guard 400 can also prevent direct contact, rubbing, chafing, and the like between the edge of pad 120 and the patient's skin. In some embodiments, the gauze may be bound or adhered together and/or adhered to an inside surface of the outer shell 410, so as to form a more cohesive and effective barrier to the edge of pad 120.

FIG. 5B illustrates an exemplary structure of an edge guard 400 containing foam 540, according to some embodiments. Pad 120 comprises hydrogel layer 340, which can meet and conform to patient's skin 320. Pad 120 additionally comprises fluid containing layer 350, which can include tortuous fluid flow paths, and insulation layer 360, which prevents loss of thermal energy to the environment. In this example, adhesive layer 420 covers pad 120 and extends over edge guard 400, as well.

Edge guard 400 can extend outwardly from the edge of pad 120 and be attached thereto. Edge guard 400 is covered by outer shell 410, and contains foam 540. For example, foam 540 may comprise silicone foam, polystyrene foam, polyurethane foam, memory foam, foam rubber, ethylene-vinyl acetate (EVA) foam, low-density polyethylene (LDPE) foam, nitrile rubber (NBR) foam, polychloroprene foam, polymeric foam, or another foam material. In various embodiments, foam filling 540 may include a single foam block or multiple foam portions, such as closed-cell extruded polystyrene foam units or the like. Because foam 540 is pliant and supple, it can absorb mechanical pressure or shocks from the edge of pad 120 and cushion the patient's skin 320, thereby increasing patient comfort and improving patient tolerance of an extended TTM treatment. Moreover, edge guard 400 containing foam 540 can function as a barrier between the edge of pad 120 and the patient's skin 320, i.e., it can prevent direct contact, rubbing, chafing, and the like between the edge of pad 120 and skin 320.

FIG. 5C illustrates an exemplary structure of an edge guard 400 containing mesh 570, according to some embodiments. Pad 120 comprises hydrogel layer 340, which can adjoin and conform to patient's skin 320. Pad 120 additionally comprises fluid containing layer 350, which can include tortuous fluid flow paths, and insulation layer 360, which prevents loss of thermal energy to the environment. In this example, adhesive layer 420 covers pad 120 and extends over edge guard 400, as well.

Edge guard 400 can extend from the edge of pad 120 and be attached thereto. Edge guard 400 is covered by outer shell 410, and contains mesh 570. For example, mesh 570 may comprise surgical mesh, polypropylene (PP), polyvinylidene fluoride (PVDF), polyethylene terephthalate (PET), polytetrafluorethylene (PTFE), nanofibrous mesh, another inorganic mesh, or another mesh material. In some examples, more than one material may be combined in the filling of edge guard 400. For example, the filling may comprise gauze balls surrounded by mesh, or some other mixture of gauze 510, foam 540, and/or mesh 570.

In some examples, the mesh filling 570 within edge guard 400 can include one or more folded, furled, crumpled, and/or compressed sheets of mesh in order to provide greater elastic response. In an example, mesh filling 570 can include one or more sheets of mesh broken or cut into multiple strips or pieces. In another example, the mesh filling may simply include multiple sheets of mesh stacked over each other. In yet another example, multiple sheets or pieces of mesh may be bound or fastened together so as to provide greater elasticity.

Because mesh 570 is soft and elastic, it can absorb mechanical pressure or shocks from the edge of pad 120 and cushion the patient's skin 320, thereby increasing patient comfort and improving patient tolerance of an extended TTM treatment. Moreover, edge guard 400 containing mesh 570 can act as a barrier between the edge of pad 120 and the patient's skin 320, i.e., it can prevent direct contact, rubbing, chafing, and the like between the edge of pad 120 and skin 320.

FIG. 6A illustrates an edge guard 600 surrounding the perimeter 610 of a pad 120, according to some embodiments. The edge guard 600 may be any of the edge guard 400 embodiments illustrated in FIGS. 4-5C and may be situated along the edge 610 of pad 120. Thus, in this example, the edge guard 600 surrounds substantially the entire perimeter 610 of pad 120. Accordingly, all edges 610 of pad 120 where pad 120 may rub or chafe against the patient's skin may be softened by edge guard 600 and made more comfortable for the patient.

FIG. 6B illustrates an edge guard 650 covering a portion 660 of the perimeter of a pad 120, according to some embodiments. The edge guard 650 may be any of the edge guard 400 embodiments illustrated in FIGS. 4-5C and, in some embodiments, the edge guard 650 only partially surrounds the perimeter of pad 120. For example, the edge guard 650 may be situated at a curve or corner 660 of pad 120, where pad 120 may have edges that are particularly rough for a patient's skin. In another example, the edge guard 650 may be attachable and/or removable from the edges of pad 120, so that a clinician can place edge guard 650 along portions of the perimeter of pad 120, as needed.

FIG. 7 illustrates an edge guard 700 in use with medical pad 120, according to some embodiments. As shown, edge guard 700 can include an adhesive layer to adhere edge guard 700 to the patient's skin, a pliant, supple filling 510 that absorbs and reduces pressure and irritation originating from edges of the medical pad on the patient, and an outer shell 410 to contain the pliant filling 510.

In some embodiments, outer shell 410 comprises a material similar to an adhesive bandage, e.g., woven fabric, plastic (such as polyvinyl chloride (PVC), polyethylene, or polyurethane), or latex. Outer shell 410 may be elastic and adhesive.

in this embodiment, the edge guard 700 contains a soft filling, such as cotton gauze, 510. In other examples, the filling can comprise soft foam or mesh (see FIGS. 5A-5C), or some combination thereof. In some embodiments, filling 510 can comprise polyester, wool, or latex, or any other material, and is not limited by the present disclosure. The filling can absorb pressure from the edges of the medical pad, and can thereby soften the impact of the medical pad on the patient's skin. Accordingly, the patient can use the medical pad for extended periods with improved comfort and fewer side effects. In some embodiments, filling 510 can include a thermally conductive material configured to conduct thermal energy between the pad and the patient.

In this example, outer shell 410 surrounds the filling 510, so as to encapsulate and contain the filling with an elastic cover. In some embodiments, the outer shell comprises a top portion 410 and a bottom portion 720. Although FIG. 7 shows a cross section of edge guard 700, i.e., filling 510 is visible in FIG. 7, it is to be understood that the outer shell can completely cover filling 510.

Alternatively, in some embodiments, outer shell 410 may only partially cover the filling. For example, outer shell 410 comprising an elastic material may cover a proximal side of edge guard 700 that faces away from the patient, while a bottom portion that contacts the patient's skin may comprise an adhesive material, like the adhesive layer 420 discussed in the example of FIG. 4. For example, the outer shell may itself be adhesive. In a further example, the bottom portion may comprise a different material (such as the adhesive layer 420) and may have different elasticity properties from outer shell 410. For example, bottom portion may adhere and/or conform to the patient's skin, but be more fixed or rigid than the top portion 410, as the portion of the patient's skin to which it adheres does not exert substantive pressure on bottom portion.

Still referring to FIG. 7, the pad 120 comprises hydrogel layer 340, fluid containing layer 350, and insulation layer 360. In this example, adhesive layer 420 covers pad 120 and extends over edge guard 700, as well. Edge guard 700 can extend outwardly from the edge of pad 120 and be attached thereto. Edge guard 700 is covered by outer shell 410, and contains gauze 510. Edge guard 700 may alternatively, or in addition, contain foam, mesh, or another material. Because gauze 510 or another cushion filling is soft and pliant, it can absorb mechanical pressure or shocks from the edge of pad 120 and cushion the patient's skin 320, thereby increasing patient comfort and improving patient tolerance of an extended TTM treatment. Moreover, edge guard 700 containing filling 510 can function as a barrier between the edge of pad 120 and the patient's skin 320.

It should be noted that in some instances, the pad 120 and any edge guard described herein may be integrally formed as a single component. Such embodiments may be advantageous to ensure that the edge guard is adequately secured to the pad 120 and placed correctly between the edge of the pad 120 and the patient's skin. However, in alternative instances, the pad 120 and an edge guard may be manufactured separately such that the edge guard is placed between the edge of the pad 120 and the patient's skin at the beginning of a targeted-temperature management procedure. Separate manufacture may be advantageous to enable retro-fitting of an edge guard to a pad 120 that had been manufactured without an edge guard but utilization of such is desired by the patient and/or clinician.

Referring now to FIGS. 8A-8B, a filter 800 is illustrated that may be included with the TTM system 100, in accordance with some embodiments. The filter 800 may be disposed in line with a TTM fluid flow path of the TTM system 100 so that the circulating TTM fluid flows through the filter 800. The filter 800 may be configured to remove (i.e., filter out) material/particles having a size of 0.2 microns or larger from the TTM fluid 112 without causing a flow restriction of the fluid 112.

The filter 800 comprises a longitudinal shape having a flow path 801 extending from a first end 802 to a second end 803. The filter 800 comprises a diffuser 810 adjacent the first end 802, a nozzle adjacent 820 the second end 803, and a body 830 extending between the diffuser 810 and the nozzle 820. Along the diffuser 810, a cross-sectional flow area of the filter 800 expands from an inlet flow area 811 to a body flow area 831 and along the nozzle 820, the cross-sectional flow area of the filter 800 contracts from the body flow area 831 to an outlet flow area 821. In some embodiments, the inlet flow area 811 and the outlet flow area 821 may be substantially equal.

In some embodiments, the body flow area 831 may be constant along the body 830. In other embodiments, the body flow area 831 may vary along a length of the body 830 such that the body flow area 831 is greater or less along middle portion of the body 830 than at the ends of the body 830. In some embodiments, the body flow area 831 may be circular.

The filter 800 comprises an inner tube 840 disposed within the body 830 extending along the length of body 830. The inner tube 840 may be coupled to the diffuser 810 at a first inner tube end 841 so that fluid 112 entering the filter 800 at the first end 802 also enters the inner tube 840 at the first inner tube end 841. The inner tube 840 may be coupled to the nozzle 820 at a second inner tube end 842 so that fluid 112 exiting the filter 800 at the second end 803 also exits the inner tube 840 at the second inner tube end 842.

The inner tube 840 comprises an inner tube flow area 845 extending the length of the inner tube 840. The inner tube flow area 845 may be greater than the inlet flow area 811 and/or the outlet flow area 821. The inner tube flow area 845 may be constant along the length of the inner tube 840. In some embodiments, the inner tube flow area 845 may vary along the length of the inner tube 840. In some embodiments, the inner tube 840 may comprise a circular cross section. The inner tube 840 and the body 830 may be configured so that the body flow area 831 comprises a combination of the inner tube flow area 845 and an annular flow area 836.

The inner tube 840 comprises a porous a circumferential wall 847. The porous wall 847 may be configured so that fluid 112 may flow through the porous wall 847, i.e., through the pores 848 of the porous wall 847. Consequently, fluid 112 may flow through the porous wall 847 from the inner tube flow area 845 to the annular flow area 836 and from the annular flow area 836 into the inner tube flow area 845.

In use, the longitudinal velocity of the fluid 112 may change along the length of the filter 800. As the volumetric fluid 112 flow through the filter is constant, the longitudinal velocity of the fluid 112 may be at least partially defined by the flow areas of the filter 800 as described below. The fluid 112 may enter the filter 800 at a first longitudinal velocity 851 and decrease along the diffuser so that the fluid 112 enters the inner tube at a second velocity 852 less than the first longitudinal velocity 851. At this point, a portion of the fluid 112 may flow through the porous wall 847 from the inner tube flow area 845 into the annular flow area 836 to divide the fluid flow into a third velocity 853 within the inner tube flow area 845 and a fourth velocity 854 within the annular flow area 836. The fourth velocity 854 may be less than the third velocity 853. A portion of the fluid 112 may then flow back into the inner tube flow area 845 from the annular flow area 836 to define a fifth velocity 855 along the inner tube flow area 845 which may be about equal to the second velocity 852. The fluid 112 may then proceed along the nozzle 820 to define a sixth velocity 856 exiting the filter 800. In some embodiments, the first velocity 851 and the sixth velocity 856 may be about equal.

The filter 800 may be configured to remove harmful bacteria and viruses from the fluid 112 using sedimentation principles. In use, the filter 800 may be oriented horizontally so that the direction of fluid flow through the filter 800 is perpendicular to a gravitational force 865. In some instances, bacteria, viruses, and other particles within the fluid 112 may have a greater density than the fluid 112 and as such may be urged by the gravitational force 865 (i.e., sink) in a direction perpendicular to the fluid flow direction. In some instances, particles within the inner tube flow area 845 may sink toward and through the porous wall 847 into the annular flow area 836. Particles within the annular flow area 836 may then sink toward an inside surface 831 of the body 830 and become trapped adjacent the inside surface 831. The geometry of the filter 800 may be configured to allow 0.2-micron bacteria/virus particles to fall out of the flow of TTM fluid 112 and become trapped along the inside surface 831.

In some embodiments, the filter 800 may be configured so that flow of fluid 112 from the inner tube flow area 845 into the annual flow area 836 may drag particles through the porous wall 847. In some embodiments, the inlet flow area 811, the inner tube flow area 845, and the annual flow area 836 may be sized so that the third velocity 853 is less than about 50 percent, 25 percent, or 10 percent of the first velocity 851 or less. In some embodiments, the body 830 and the inner tube 840 may be configured so that the fourth velocity 854 is less than the third velocity 853. In some embodiments, the fourth velocity 854 may less than about 50 percent, 25 percent, or 10 percent of the third velocity 853 or less.

In some embodiments, the filter 800 may be configured so that the flow within the inner tube flow area 845 is laminar flow, i.e., so that the velocity of the fluid flow adjacent to or in close proximity to an inside surface 841 of the porous wall 847 is less than the velocity at a location spaced away from the inside surface 841. In such an embodiment, the particles may more readily sink toward and through the porous wall 847.

In some embodiments, the filter 800 may be configured so that the fluid flow within the annual flow area 836 is laminar flow, i.e., so that the velocity of the fluid flow adjacent to or in close proximity to inside surface 831 of the body 830 is less than the velocity at a location spaced away from the inside surface 831. In such an embodiment, the particles may more readily sink toward and be trapped along the inside surface 831.

The filter 800 may comprise three components including the inner tube 840 an inner body shell 838, and an outer body shell 839. Each of the three components may be formed via the plastic injection molding process. Assembly of the filter 800 may include capturing the inner tube 840 within the inner body shell 838 and the outer body shell 839 and sliding the inner body shell 838 into the outer body shell 839 wherein the fit between the inner body shell 838 and the outer body shell 839 is an interference fit.

In some embodiments, the filter 800 may be disposed within the pad 120. FIG. 8C shows a detail cross-sectional view of the pad 120 including the filter 800 disposed within the fluid containing layer 350. The filter 800 is coupled in line with an internal flow path 860 within the fluid containing layer 350 so that fluid 112 circulating within the pad 120 passes through the filter 800. The filter 800 may be sized so that the inlet flow area 811 and the outlet flow area 821 are similar to a cross-sectional flow area of the internal flow path 860 within the fluid containing layer 350. The internal flow path 860 may be comprised of tubing (e.g., similar to the fluid delivery lines 140) that is disposed within the fluid containing layer 350. In such embodiments, the tubing of the internal flow path 860 receives the fluid 112 from a fluid delivery line 140 at an inlet port. The fluid 112 flows through the tubing of the internal flow path 860, passing through the filter 800, toward an outlet port, at which point the fluid 112 exits the pad 120 and is received by a second fluid delivery line 140.

In some embodiments, a thickness of the fluid containing layer 350 may increase adjacent the filter 800 to accommodate a body diameter 864 of the filter 800. To further accommodate the body diameter 864, the insulation layer 360 and/or the thermal conduction layer 340 may comprise internal depressions 862, 863, respectively.

In some embodiments, one or more filters 800 may be disposed in line with the flow of fluid 112 at other locations of the TTM system 100. In some embodiments, one or more filters 800 may be disposed within the TTM module 110. In some embodiments, one or more filters 800 may be disposed in line with one or more of the fluid delivery lines 140. In some embodiments, the filter 800 may be disposed in line with a fluid conduit of the pad external to the fluid containing layer 350 such as a conduit extending between a pad connector and the pad 120.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. A medical pad for exchanging thermal energy with a patient, the medical pad comprising:
- a flexible upper sheet;
- a flexible base member interconnected to the flexible upper sheet to define a fluid containing layer between the flexible base member and the flexible upper sheet;
- an edge guard situated along an edge of the flexible upper sheet, wherein the edge guard extends outwardly from the edge of the flexible upper sheet, the edge guard including:
  - a pliant cover including a top cover portion and a bottom cover portion, and
  - a cushion filling contained within the pliant cover and configured to reduce pressure from the edge of the flexible upper sheet on a skin of the patient; and
- an adhesive surface disposed on a skin-contacting side of the flexible upper sheet and the top cover portion of the edge guard, wherein the adhesive surface is adapted for releasable adhesive contact with the skin of the patient.

2. The medical pad of claim 1, wherein the cushion filling of the edge guard comprises a thermally conductive material configured to conduct thermal energy between the fluid containing layer and the patient.

3. The medical pad of claim 1, wherein the edge guard is configured to conform to a contour of the skin of the patient, so as to provide a direct path for the edge guard to conduct the thermal energy.

4. The medical pad of claim 1, wherein the cushion filling comprises one or more of gauze filling, foam filling, or mesh filling.

5. The medical pad of claim 1, wherein the pliant cover comprises one or more of woven fabric, polyvinyl chloride (PVC), polyethylene, polyurethane, another plastic, and latex.

6. The medical pad of claim 1, wherein the edge guard is situated along the edge, wherein the edge substantially surrounds a perimeter of the flexible upper sheet, and the edge guard substantially surrounds the perimeter of the flexible upper sheet.

7. The medical pad of claim 1, further comprising a conformable, thermally conductive layer of a hydrogel material.

8. The medical pad of claim 1, wherein the flexible base member includes a plurality of dimples defining a plurality of tortuous fluid flow paths.

9. The medical pad of claim 8, wherein the plurality of dimples are of a predetermined configuration comprising one or more of:
- a truncated cone configuration,
- a cylindrical configuration, and
- an elongated, truncated pyramid configuration.

10. The medical pad of claim 8, wherein:
- the plurality of dimples are arranged in a predetermined staggered pattern on an upper surface of the flexible base member,
- a lower smooth surface of the flexible upper sheet is supported at a plurality of points of contact with the plurality of dimples, and
- the plurality of dimples are staggered in at least two transverse directions on the upper surface of the flexible base member.

11. The medical pad of claim 10, wherein the predetermined staggered pattern comprises offset rows and columns.

12. The medical pad of claim 11, wherein the plurality of dimples within adjacent rows and adjacent columns are offset from one another by sixty degrees.

13. The medical pad of claim 8, wherein the plurality of dimples are arranged in a herringbone pattern.

14. The medical pad of claim 8, wherein the flexible base member is formed to integrally define the plurality of dimples.

15. The medical pad of claim 1, further comprising a filter disposed in line with a fluid flow path providing a fluid to the medical pad.

16. The medical pad of claim 15, wherein the filter comprises a porous wall disposed parallel to a flow direction of the fluid along the fluid flow path.

17. The medical pad of claim 15, wherein the filter is attached to the medical pad.

18. The medical pad of claim 15, wherein the filter is disposed within the fluid containing layer of the medical pad.

19. A medical pad for exchanging thermal energy with a patient, the medical pad comprising:
- a flexible base member of foam construction having a plurality of integrally defined dimples;
- a flexible film interconnected to the flexible base member to define a fluid containing layer between the flexible base member and the flexible film, wherein the plurality of integrally defined dimples define tortuous fluid flow paths within the fluid containing layer;
- a thermally conductive layer laminated to one side of the flexible film;
- an edge guard situated along an edge of the thermally conductive layer, wherein the edge guard extends outwardly from the edge of the thermally conductive layer, the edge guard including:
  - a pliant cover including a top cover portion and a bottom cover portion, and a cushion filling contained within the pliant cover and configured to reduce pressure from the edge of the thermally conductive layer on a skin of the patient; and an adhesive surface disposed on the thermally conductive layer and the top cover portion of the edge guard, wherein the adhesive surface is adapted for releasable adhesive contact with the skin of the patient.

20. The medical pad of claim 19, wherein the cushion filling of the edge guard comprises a thermally conductive material configured to conduct thermal energy between the fluid containing layer and the patient.

21. The medical pad of claim 19, wherein the edge guard is configured to conform to a contour of the skin of the patient, so as to provide a direct path for the edge guard to conduct the thermal energy.

22. The medical pad of claim 19, wherein the cushion filling comprises one or more of gauze filling, foam filling, or mesh filling.

23. The medical pad of claim 19, wherein the pliant cover comprises one or more of woven fabric, polyvinyl chloride (PVC), polyethylene, polyurethane, another plastic, and latex.

24. The medical pad of claim 19, wherein the edge guard substantially surrounds a perimeter of the thermally conductive layer.

25. The medical pad of claim 19, wherein the thermally conductive layer comprises a conformable hydrogel material.

26. The medical pad of claim 19, wherein the plurality of integrally defined dimples defining the tortuous fluid flow paths are of a predetermined configuration comprising one or more of:

a truncated cone configuration, a cylindrical configuration, and an elongated, truncated pyramid configuration.

27. The medical pad of claim 19, further comprising a filter disposed in line with a fluid flow path providing a fluid to the medical pad.

28. The medical pad of claim 27, wherein the filter comprises a porous wall disposed parallel to a flow direction of the fluid along the fluid flow path.

29. The medical pad of claim 27, wherein the filter is attached to the medical pad.

30. The medical pad of claim 27, wherein the filter is disposed within the fluid containing layer of the medical pad.

* * * * *